(12) United States Patent
De La Torre et al.

(10) Patent No.: US 7,414,132 B2
(45) Date of Patent: Aug. 19, 2008

(54) OPIOID RECEPTOR ANTAGONISTS

(75) Inventors: Marta Garcia De La Torre, Alcobendas Madrid (ES); Nuria Diaz Buezo, Alcobendas Madrid (ES); Prabhakar Kondaji Jadhav, Zionsville, IN (US); Charles Howard Mitch, Columbus, IN (US); Concepcion Pedregal-Tercero, Alcobendas Madrid (ES)

(73) Assignee: Eli Lilly and Company, Indianapolis, IN (US)

( * ) Notice: Subject to any disclaimer, the term of this patent is extended or adjusted under 35 U.S.C. 154(b) by 90 days.

(21) Appl. No.: 10/581,178

(22) PCT Filed: Dec. 15, 2004

(86) PCT No.: PCT/US2004/039766

§ 371 (c)(1),
(2), (4) Date: May 31, 2006

(87) PCT Pub. No.: WO2005/066164

PCT Pub. Date: Jul. 21, 2005

(65) Prior Publication Data

US 2007/0112036 A1    May 17, 2007

(30) Foreign Application Priority Data

Dec. 22, 2003  (EP)  ................... 03380303

(51) Int. Cl.
*C07D 213/00* (2006.01)
*C07D 231/56* (2006.01)
*C07D 261/20* (2006.01)
*C07D 413/00* (2006.01)
*C07D 498/00* (2006.01)

(52) U.S. Cl. .................. 546/1; 548/241; 548/361.1

(58) Field of Classification Search ................. None
See application file for complete search history.

(56) References Cited

FOREIGN PATENT DOCUMENTS

| WO | WO 98/09625 | 3/1998 |
|---|---|---|
| WO | WO 00/40560 | 7/2000 |
| WO | WO 02/38544 | 5/2002 |
| WO | WO 02/078693 | 10/2002 |
| WO | WO 2004/026305 | 4/2004 |
| WO | WO 2004/080968 | 9/2004 |
| WO | WO 2004/080996 | 9/2004 |

OTHER PUBLICATIONS

Patani and LaVoie. Chemical Reviews, 1996, 96, 3147-76.*
Vippagunta et al. Advanced Drug Delivery Reviews, 2001, 48, 3-26.*
Daintith, J. A Dictionary of Chemistry, 1996, pags 157 and 353-54.*

* cited by examiner

*Primary Examiner*—James O. Wilson
*Assistant Examiner*—Noble Jarrell
(74) *Attorney, Agent, or Firm*—John C. Demeter; Francis O. Ginah

(57) ABSTRACT

A compound of the formula (I); wherein the variables $X_1$ to $X_{10}$, $R^1$ to $R^7$ including $R^{3'}$, E, W, v, y, z, A and B are as described, or a pharmaceutically acceptable salt, solvate, enantiomer, racemate, diastereomer or mixtures thereof, useful for the treatment, prevention or amelioration of obesity and Related Diseases is disclosed.

2 Claims, No Drawings

OPIOID RECEPTOR ANTAGONISTS

The present invention is in the field of medicinal chemistry. The invention relates specifically to compounds useful as opioid antagonists, methods of treatment, methods of using, and pharmaceutical compositions thereof.

BACKGROUND

Three types of opioid receptors, mu, kappa, and delta opioid receptors are generally reported. Recent evidence points to the interactions between receptor dimer combinations of mu, kappa and/or delta receptors (called heterodimers) as also contributing to opioid activity. Opioid receptors and their normal regulation or lack thereof, has been implicated in disease states including irritable bowel syndrome, nausea, vomiting, pruritic dermatoses, depression, smoking and alcohol addiction, sexual dysfunction, stroke and trauma in animals. Therefore it is not surprising that the ability to antagonistically bind opioid receptors has been shown to produce ameliorative, preventative and/or treatment effects in animals including humans afflicted with one or more of these disease states.

More recently, certain antagonists of the opioid receptors have been found to increase metabolic energy consumption, and reduction of weight in obese rats while maintaining muscle mass. These findings indicate that an effective opioid antagonist may be useful in preventing, treating and/or ameliorating the effect of obesity. Considering the percentage of the population that is obese in Western societies and the indirect costs associated with treating the effects and symptoms of obesity and Related Diseases, the importance of these findings cannot be overstated.

Though many opioid antagonists have been disclosed, the search continues for alternative and/or improved or more effective antagonists having an overall benefit to the patient with little or no major side effects. U.S. Pat. No. 4,891,379 disclosed phenylpiperidine opioid antagonists useful for the treatment of diabetes and obesity. In particular, U.S. Pat. No. 4,891,379 disclosed the compound LY 255582 represented by the structure:

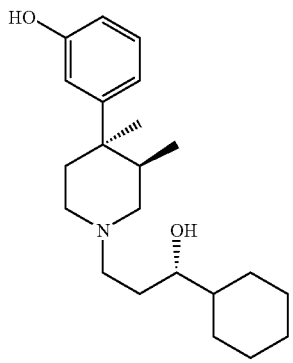

U.S. Pat. No. 4,191,771 also disclosed compounds useful as opioid antagonists. Also, bicyclic analogs of phenyl piperidine have been prepared and reported as opioid antagonists in Wentland, et al., Biorganic and Medicinal Chemistry Letters 11 (2001) 623-626; see also Wentland, et al., Bioorganic and Medicinal Chemistry Letters 11 (2001) 1717-1721. Finally, European Patent application number EP 1 072592A2 filed May 18, 2000, discloses phenylpiperidine compounds of formula 1

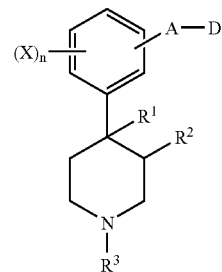

wherein A, D, $R^1$, $R^2$, $R^3$, X, and n have meanings given in the description, which are useful in the prophylaxis and in the treatment of diseases mediated by opioid receptors such as pruritus.

U.S. Pat. No. 6,140,352 and related patents disclose the compound of formula Formula 1

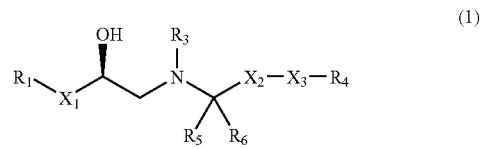

wherein the variables $X_1$, $X_2$, $X_3$ $R_1$, $R_3$, $R_4$, $R_5$ and $R_6$ are as described therein, as agonists of the beta adrenergic receptor useful for the treatment of diabetes and obesity.

Regardless of these and other disclosures of compounds useful as opioid receptor antagonists, or useful for the treatment of obesity, and/or diabetes by other mechanisms, there remains an unmet medical need for a safe, effective and/or alternate treatment or prophylaxis of diseases associated with opioid receptors, particularly obesity and Related Diseases.

SUMMARY OF THE INVENTION

The present invention provides a compound of the formula (I)

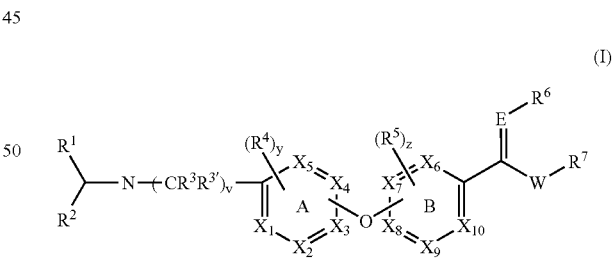

wherein
each of $X_1$, $X_2$, $X_3$, $X_4$, $X_5$, $X_6$, $X_7$, $X_8$, $X_9$ and $X_{10}$ is C, CH, or N; provided that each of rings A or B has no more than 2 nitrogen atoms;

E is O or N; provided that when E is O, $R^6$ is absent from E-$R^6$; and further provided that when E is O and $R^6$ is absent, then W is not $NR^7$;

W is O or $NR^7$;

v is 1, 2, or 3;

$R^1$ and $R^2$ are independently selected from hydrogen, $C_1$-$C_8$ alkyl, $C_2$-$C_8$ alkenyl, $C_2$-$C_8$ alkynyl, $C_3$-$C_8$ cycloalkyl, aryl, $C_1$-$C_{10}$ alkylaryl, $C(O)C_1$-$C_8$ alkyl, $CO(O)C_1$-$C_8$ alkyl, $SO_2C_1$-$C_8$ alkyl, $SO_2C_1$-$C_{10}$ alkylaryl, $C_1$-$C_8$ alkylheterocyclic, $SO_2C_1$-$C_8$ alkylheterocyclic, $C_1$-$C_{10}$ alkylcycloalkane, $C_1$-$C_8$ alkoxyalkyl, $(CH_2)_nC(O)OR^8$, $(CH_2)_nC(O)R^8$, $(CH_2)_mC(O)NR^8R^8$, and $(CH_2)_mNSO_2R^8$; wherein each of the alkyl, alkenyl, cycloalkyl, heterocyclic and aryl groups are optionally substituted with one to five groups independently selected from oxo, $C_1$-$C_8$ alkyl, $C_2$-$C_8$ alkenyl, phenyl, $C_1$-$C_8$ alkylaryl, $C(O)C_1$-$C_8$ alkyl, $CO(O)C_1$-$C_8$ alkyl, $C_1$-$C_8$ alkoxy, $SO_2C_1$-$C_8$ alkyl, $SO_2C_1$-$C_8$ alkylaryl, $SO_2C_1$-$C_8$ alkylheterocyclic, $C_1$-$C_{10}$ alkylcycloalkane, $(CH_2)_nC(O)OR^8$, and $(CH_2)_nC(O)R^8$; and wherein $R^1$ and $R^2$ may optionally combine together to form a 4, 5, 6, or 7-membered nitrogen-containing heterocycle which nitrogen-containing heterocycle is optionally substituted with 1, 2, or 3 substitutents independently selected from the group consisting of oxo, amino, $C_1$-$C_8$ alkyl, $C_2$-$C_8$ alkenyl, $C_2$-$C_8$ alkynyl, $C_1$-$C_8$ alkoxy, phenyl, $C_1$-$C_8$ alkylaryl, $C(O)C_1$-$C_8$ alkyl, $CO(O)C_1$-$C_8$ alkyl, halo, and $C_1$-$C_8$ haloalkyl;

$R^3$ and $R^{3'}$ are each independently selected from hydrogen, $C_1$-$C_8$ alkyl, $C_2$-$C_8$ alkenyl, $C_2$-$C_8$ alkynyl, phenyl, aryl, $C_1$-$C_8$ alkylaryl;

$R^4$ and $R^5$ are each independently selected from hydrogen, $C_1$-$C_8$ alkyl, $C_2$-$C_8$ alkenyl, $C_2$-$C_8$ alkynyl, $C_1$-$C_8$ alkoxy, halo, $C_1$-$C_8$ haloalkyl, phenyl, aryl, $C_1$-$C_8$ alkylaryl, $(CH_2)_m$ $NSO_2C_1$-$C_8$ alkyl, $(CH_2)_mNSO_2$phenyl, $(CH_2)_m$ $NSO_2$aryl, —$C(O)C_1$-$C_8$ alkyl, and —$C(O)OC_1$-$C_8$ alkyl; wherein each $R^4$ and $R^5$ is attached to its respective ring only at carbon atoms, and wherein y is 0, 1, 2, or 3; and wherein z is 0, 1, 2, or 3;

$R^6$ and $R^7$ are each independently selected from hydrogen, $C_1$-$C_8$ alkyl, $C_2$-$C_8$ alkenyl, $C_2$-$C_8$ alkynyl, $C(O)C_1$-$C_8$ alkyl, hydroxy, $C_1$-$C_8$ alkoxy, aryl, $C_1$-$C_8$ alkylaryl, $C_3$-$C_8$ cycloalkyl, $C_1$-$C_8$ alkylheterocyclic, $C_1$-$C_{10}$ alkylcycloalkyl, —$NHC_1$-$C_8$ alkyl, $(CH_2)_nC(O)OR^8$, $(CH_2)_nC(O)R^8$, $(CH_2)_mC(O)NR^8R^8$, and $(CH_2)_mNSO_2R^8$; wherein each of the alkyl, alkenyl, cycloalkyl, heterocyclic, and aryl groups is optionally substituted with one to 3 groups independently selected from $C_1$-$C_8$ alkyl, $C_2$-$C_8$ alkenyl, phenyl, and $C_1$-$C_8$ alkylaryl; and wherein $R^6$ and $R^7$ optionally combine together to form a 5, 6, or 7-membered nitrogen-containing heterocycle with E and W; and wherein the nitrogen containing heterocycle is optionally substituted with 1-2 groups independently selected from the group consisting of oxo, amino, $C_1$-$C_8$ alkyl, $C_2$-$C_8$ alkenyl, $C_2$-$C_8$ alkynyl, phenyl, $C_1$-$C_8$ alkylaryl, $C(O)C_1$-$C_8$ alkyl, $CO(O)C_1$-$C_8$ alkyl, hydroxy, $C_1$-$C_8$ alkoxy, halo, and haloalkyl;

$R^8$ is hydrogen, $C_1$-$C_8$ alkyl, $C_2$-$C_8$ alkenyl, $C_5$-$C_8$ alkylaryl, $(CH_2)_mNSO_2C_1$-$C_8$ alkyl, $(CH_2)_mNSO_2$aryl, —$C(O)C_1$-$C_8$ alkyl, or —$C(O)OC_1$-$C_8$ alkyl; n is 0, 1, 2, or 3; and m is 1, 2 or 3;

or a pharmaceutically acceptable salt, solvate, enantiomer, racemate, diastereomers or mixtures thereof.

The present invention also provides a pharmaceutical formulation comprising a compound of formula I in association with a carrier, diluent and/or excipient.

The present invention also relates to a method for the treatment and/or prophylaxis of obesity and Related Diseases including eating disorders (bulimia, anorexia nervosa, etc.), diabetes, diabetic complications, diabetic retinopathy, sexual/reproductive disorders, depression related to obesity, anxiety related to obesity, epileptic seizure, hypertension, cerebral hemorrhage, congestive heart failure, sleeping disorders, atherosclerosis, stroke, hyperlipidemia, hypertriglycemia, hyperglycemia, hyperlipoproteinemia, substance abuse, drug overdose, compulsive behavior disorders (such as paw licking in dogs), metabolic diseases, and addictive behaviors such as for example, gambling, and alcoholism, comprising administering a therapeutically effective amount of a compound of formula I or a pharmaceutically acceptable salt, solvate, enantiomer, racemate, diastereomer or mixture of diastereomers thereof.

The present invention provides a compound of formula (I) useful for the manufacture of a medicament for the treatment, prevention and/or amelioration of symptoms associated with obesity and Related Diseases.

In another embodiment, the present invention provides a compound of formula I or a pharmaceutically acceptable salt, solvate, enantiomer, racemate, diastereomer or mixture thereof, useful as an appetite suppressant.

In another embodiment, the present invention provides a method of achieving weight loss while maintaining or minimizing the loss of lean muscle mass, comprising administering a compound of formula I or a pharmaceutically acceptable salt, solvate, enantiomer, racemate, diastereomer or mixtures thereof, to a patient in need thereof.

DETAILED DESCRIPTION OF THE INVENTION

As used herein the term "obesity" has its commonly understood meaning such as "excessively fat" and includes the clinical designation of being obese as defined in and by the medical literature and brochures of support or public health organizations. For example, *Dorland's Illustrated Medical Dictionary* (29$^{th}$ edition, W.B. Saunders Company, Philadelphia USA.) defines obesity as an increase in bodyweight beyond the limitation of skeletal and physical requirements, as the result of an excessive accumulation of fat in the body." Because the decision of suitability for treatment of a patient with compound(s) of the present invention to a patient is to be made by a qualified physician or care giver, the patient is inherently deemed suitable or obese by the administering caregiver.

As used herein, the term "patient" includes human and non-human animals such as companion animals (dogs and cats) and livestock animals.

The preferred patients of treatment, amelioration and/or prevention of obesity and Related Diseases are human.

The terms "treating" and "treat", as used herein, include their generally accepted meanings, i.e., preventing, prohibiting, restraining, alleviating, ameliorating, slowing, stopping, or reversing the progression or severity of a pathological condition, or sequela thereof, described herein.

The terms "ameliorating" "preventing", "prevention of", "prophylaxis", "prophylactic" and "prevent" are used herein interchangeably and refer to reducing the severity of the symptoms associated with obesity and Related Diseases in a patient afflicted with same or reducing the likelihood that the recipient of a compound of formula I will incur or develop any of the pathological conditions, or sequela thereof, described herein.

As used herein, the term "effective amount" is synonymous with "effective dose" and means an amount of a compound of formula I that is sufficient in one or more administrations to prevent, ameliorate or treat a condition, or detrimental effects thereof, herein described, or an amount of a compound of formula I that is sufficient for antagonizing the opioid receptors to achieve the objectives of the invention.

The term "pharmaceutically acceptable" is used herein as an adjective and means substantially non-deleterious to the recipient patient.

The term "Active Ingredient" as used herein means a compound of formula I or a combination of compounds of formula I or a combination of a compound of formula I and a co-antagonist of the opioid receptor or a combination of a compound of formula I in addition to other effective anti-obesity, weight loss or anti-diabetic agent.

The term "formulation", as in pharmaceutical formulation, or "pharmaceutical composition" is intended to encompass a product comprising the Active Ingredient (as defined supra), and the inert ingredient(s) that make up the carrier, or other components of the drug as administered, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical formulations of the present invention encompass any effective composition made by admixing a compound of the present invention and a pharmaceutical carrier. The pharmaceutical formulations of the present invention also encompass a compound of the formula I and a pharmaceutically effective co-antagonist of opioid receptors useful for the treatment and/or prevention of obesity or Related Diseases.

The term "Related Diseases" as used herein refers to such symptoms, diseases or conditions caused by, exacerbated by, induced by, related to, or adjunct to the condition of being obese. Such diseases, conditions and/or symptoms include but are not limited to eating disorders (bulimia, anorexia nervosa, etc.), diabetes, diabetic complications, diabetic retinopathy, sexual/reproductive disorders, obesity related depression, obesity related anxiety, epileptic seizure, hypertension, cerebral hemorrhage, congestive heart failure, sleeping disorders, metabolic diseases and symptoms thereof, atherosclerosis, stroke, hyperlipidemia, hypertriglycemia, hyperglycemia, and hyperlipoproteinemia. As used herein the terms obesity related depression and obesity related anxiety are conditions of depression and anxiety respectively, that are symptomatic of certain obese patients and possibly brought on by the awareness or self-consciousness of the condition of being obese and/or possibly coupled with the real or perceived reaction to acceptance or disapproval by the certain individual, individuals or the public at large. Obesity related depression or anxiety may generally be alleviated or treated adjunctively with antidepressants such as Prozac, Zoloft and the like while the underlying condition of being obese or overweight is treated and/or prevented by administration of a compound of formula I.

The term "suitable solvent" refers to any solvent, or mixture of solvents, inert to the ongoing reaction that sufficiently solubilizes the reactants to afford a medium within which to effect the desired reaction.

The term "mutual solvent" means a solvent that is used to dissolve sufficiently, two or more components of a reaction or mixture separately prior to reaction or mixing, that is a solvent common to more than one reagents or components of a mixture.

The term "nitrogen containing heterocycle" refers to a aromatic or non-aromatic, monocyclic or bicyclic ring system which is a 4, 5, 6, or 7-member ring system containing 1, 2 or 3 nitrogen atoms in addition to the carbon atoms completing the ring size, or a combination of 1 nitrogen atom and 1, or 2 atoms selected from oxygen, and sulfur in addition to the appropriate number of carbon atoms completing the ring size. A nitrogen containing heterocycle as used here may have 0, 1, 2 or 3 double bonds.

The term "$C_1$-$C_8$ alkyl" or "$C_{1-8}$ alkyl" refers to and includes all groups, structural isomers and/or homologues of alkyl groups having from 1 to 8 carbon atoms. When the term $C_1$-$C_8$ alkyl precedes or prefixes another group, the term $C_1$-$C_8$ alkyl, only limits the number of carbon atoms in the alkyl component. For example $C_1$-$C_8$ alkylaryl, means an aryl group having a $C_1$-$C_8$ alkyl group substituent such that the number of carbon atoms in the group $C_1$-$C_8$ alkylaryl is effectively the number of carbon atoms in the aryl group plus the number of carbon atoms in the $C_1$-$C_8$ alkyl group. Similarly, the term "$C_1$-$C_8$ alkylcycloalkyl" refers to a cycloalkane group having a $C_1$-$C_8$ alkyl substituent, and wherein the entire group $C_1$-$C_8$ alkylcycloalkane may itself be a substituent attached at either the alkyl group or the cycloalkyl group to a substrate. The definition and usage applies equally to other homologues of $C_1$-$C_8$ such as for example, $C_1$-$C_7$, $C_1$-$C_6$ etc. In general, where necessary a dash (-) has been placed by certain groups that may require it to indicate the point of attachment for clarity. Nonetheless, the lack of a dash (-) does not negate an otherwise obvious point(s) of attachment known to one of skill in the art.

The term "cycloalkane" or "cycloalkyl" means cycloalkanes having from 3 to 8 carbon atoms i.e. from cyclopropane to cyclooctane.

The term "hal" or "halo" as used herein refers to a halogen including fluorine, chlorine, bromine or iodine.

The term "haloalkane" or "haloalkyl" means haloalkanes having from 1 to 8 carbon atoms, and from 1 to 3 halogen atoms as allowed by valency considerations. Examples include chloroethyl, trifluoromethyl, 2-chloropropyl, etc.

As used herein the terms "alkenyl" refers to straight or branched carbon atoms having 1 or 2 carbon-carbon double bonds.

As used herein the terms "alkynyl" refers to straight or branched carbon atoms having 1 or 2 carbon-carbon triple bonds.

As used herein the term "alkoxy" refers to the group "O-alkyl" wherein alkyl is as defined previously.

The term "aryl" as used herein refers to compounds or groups having the Huckel 4n+2 pi electron arrangement and includes for example, phenyl, naphthyl, tetrahydronaphthyl, benzothiophene, etc, but excludes carbazoles and other fused tricyclic ring structures.

As used herein the term "aroxy" or "aryloxy" refers to the group "O-aryl" wherein aryl is as defined previously.

As used herein the term "fused bicyclic," means a fused cycloalkane ring system wherein each ring has from 4 to 8 carbon atoms (i.e. $C_8$-$C_{16}$ fused bicyclic) and the fused ring system has from 0 to 3 bridgehead carbon atoms. One or both of the fused rings may contain zero or one double bond. Examples of fused bicyclics include but are not limited to bicyclo[2,2,1]heptyl, bicyclo[2,2,1]heptenyl.

As used herein the terms "heterocyclic" or "heterocyclyl" or "heterocycle" are used interchangeably and has its usual meaning and includes mono, bi or tricyclic or spirocyclic heterocyclic groups unless otherwise specified. Heterocycles as used herein may contain 1, 2, or 3 heteroatoms selected independently from nitrogen, oxygen or sulfur, unless otherwise specified. Examples of heterocyclic groups applicable to the present invention include but are not limited to pyranyl, piperazinyl, pyrrolidinyl, azapanyl, azaflorenyl, isoquinolinyl, indolinyl, thiophenyl, benzthiopheneyl, oxazolyl, morphorlinyl, thiomorphorlinyl, and piperidinyl. Each of the heterocyclic groups may be mono or di substituted or as specified with substituents such as alkyl, cycloalkyl, aryl, among others as defined. Furthermore, substitution may be at the 1-position or on the heteroatom as in piperazine, pyrrolidine or at a carbon atom or both.

As used herein, the term "protecting group" refers to a group useful for masking reactive sites in a molecule to enhance the reactivity of another group or allow reaction at another desired site or sites following which the protecting group may be removed. Protecting groups are usually used to protect or mask groups including but not limited to —OH, —NH, and —COOH. Suitable protecting groups are known to one of skill in the art and are described in Protecting groups in Organic Synthesis, 3$^{rd}$ edition, Greene, T. W.; Wuts, P. G. M. Eds., John Wiley and Sons, New York, 1999.

As used herein, the term "solvate" is a form of the compound of the invention wherein a crystal or crystals of a compound of the invention have been formed from a stoichiometric or non-stoichiometric amount of the compound of formula I and a solvent. Typical solvating solvents include for example, water, methanol, ethanol, acetone and dimethylformamide.

In those instances where a compound of the invention possesses acidic or basic functional groups, various salts may be formed which are more water soluble and/or more physiologically suitable than the parent compound. Representative pharmaceutically acceptable salts, include but are not limited to, the alkali and alkaline earth salts such as lithium, sodium, potassium, calcium, magnesium, aluminum and the like. Salts are conveniently prepared from the free acid by treating the acid in solution with a base or by exposing the acid to an ion-exchange resin.

Included within the definition of pharmaceutically acceptable salts are the relatively non-toxic, inorganic and organic base addition salts of compounds of the present invention, for example, ammonium, quaternary ammonium, and amine cations, derived from nitrogenous bases of sufficient basicity to form salts with the compounds of this invention (see, for example, S. M. Berge, et al., "Pharmaceutical Salts," *J. Phar. Sci.*, 66: 1-19 (1977)). Moreover, the basic group(s) of the compound of the invention may be reacted with suitable organic or inorganic acids to form salts such as acetate, benzenesulfonate, benzoate, bicarbonate, bisulfate, bitartrate, borate, hydrobromide, camsylate, carbonate, clavulanate, citrate, chloride, edetate, edisylate, estolate, esylate, fluoride, fumarate, gluceptate, gluconate, glutamate, glycolylarsanilate, hexylresorcinate, hydrochloride, hydroxynaphthoate, hydroiodide, isothionate, lactate, lactobionate, laurate, maleate, mandelate, mesylate, methylbromide, methylnitrate, methylsulfate, mucate, napsylate, nitrate, oleate, oxalate, palmitate, pantothenate, phosphate, polygalacturonate, salicylate, stearate, subacetate, succinate, tannate, tartrate, tosylate, trifluoroacetate, trifluoromethane sulfonate, and valerate. Preferred salts for the purpose of the invention include the hydrochloride salt, the hydrobromidse salt, the bisulfate salt, the methane sulfonic acid salt, the p-toluenesulfonic acid salt, bitartrate, the acetate and the citrate salt.

A compound of the invention as illustrated by formula I may occur as any one of its positional isomers, stereochemical isomers or regio-isomers, all of which are objects of the invention. Certain compounds of the invention may possess one or more chiral centers, and thus, may exist in optically active forms. Likewise, when the compounds contain an alkenyl or alkenylene group, there exist the possibility of cis- and trans-isomeric forms of the compounds. The R- and S-isomers and mixtures thereof, including racemic mixtures as well as mixtures of enantiomers or cis- and trans-isomers, are contemplated by this invention. Additional asymmetric carbon atoms can be present in a substituent group such as an alkyl group. All such isomers as well as the mixtures thereof are intended to be included in the invention. If a particular stereoisomer is desired, it can be prepared by methods well known in the art by using stereospecific reactions with starting materials which contain the asymmetric centers and are already resolved or, alternatively by methods which lead to mixtures of the stereoisomers and subsequent resolution by known methods. For example, a racemic mixture may be reacted with a single enantiomer of some other compound i.e. a chiral resolving agent. This changes the racemic form into a mixture of stereoisomers and diastereomers, because they have different melting points, different boiling points, and different solubilities and can be separated by conventional means, such as crystallization.

PCT international application WO 02/078693 A2 published Oct. 10, 2002 discloses compounds of the formula

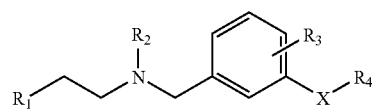

wherein $R_1$, $R_2$, $R_3$, $R_4$ and X are as described therein, as antagonists of the 5-HT$_6$ receptor for the treatment of disorders including cognitive disorders, age related disorders, mood disorders, psychosis, etc. The compounds of the present invention however, are useful for the treatment and/or prevention of obesity and Related Diseases. The compounds of the present invention have also shown inhibition of orexigenic effects, and are thus useful as appetite suppressants either as a single therapy or as combination therapy in conjunction with exercise and other effective appetite suppressing or weight loss medications.

PREFERRED EMBODIMENTS OF THE INVENTION

A compound of formula I preferably exists as the free base or a pharmaceutically acceptable salt. More preferred is the hydrochloride salt, the bisulfate salt, mesylate or the oxalic acid salt of the compound of formula I.

Preferred embodiments of the compound of formula I include the substructures Ia, Ib and Ic as shown below:

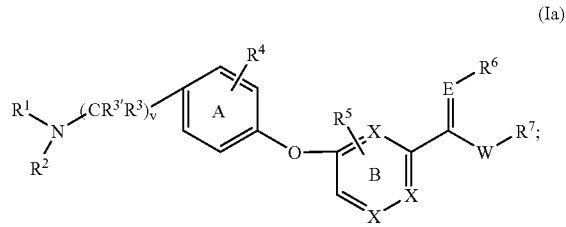

(Ia)

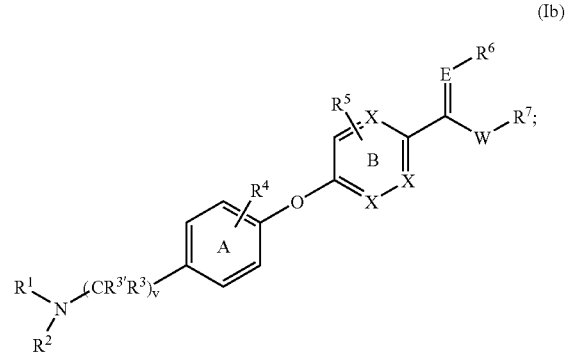

(Ib)

-continued

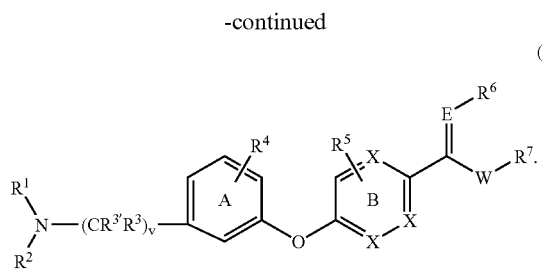
(Ic)

For the Groups $R^1$ and $R^2$

Preferred $R^1$ and $R^2$ groups are independently selected from the group consisting of hydrogen, methyl, ethyl, propyl, pentyl, phenyl, naphthyl, benzothiophene, and isopropyl.

Also preferred are $R^1$ and $R^2$ groups independently selected from the group consisting of methyl, ethyl, propyl, isopropyl, phenyl,

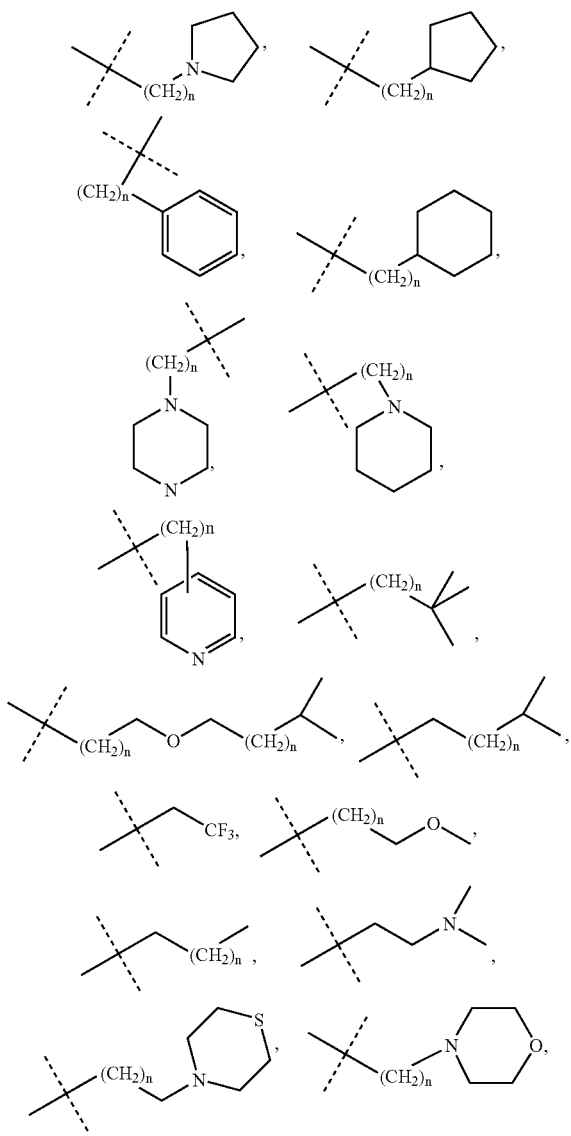

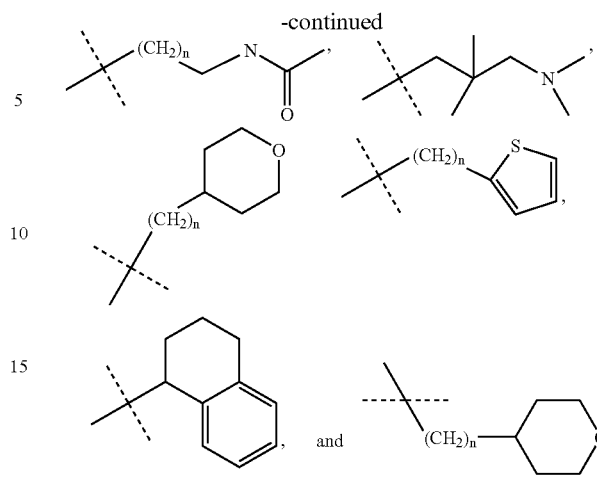

each of which is optionally substituted with a group selected from the group consisting of halogen, $C_1$-$C_8$ alkyl, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or —$C_1$-$C_4$ alkylheterocycle; or combine with a group selected from $C_1$-$C_8$ alkyl, halogen, $C_1$-$C_8$ haloalkyl, $C_1$-$C_8$ thioalkyl, $C_1$-$C_8$ alkylamino, phenyl, $C_1$-$C_8$ alkylsubstituted phenyl, $C_4$-$C_8$ heterocycle or $C_1$-$C_4$ alkyl heterocycle to form a substituted or unsubstituted bicycle or tricycle, and wherein n is preferably 1, 2, or 3. The broken (dashed) bond indicates the point of attachment to the substrate.

Also preferred are $R^1$ and $R^2$ groups that combine with each other or with 1 or 2 atoms adjacent to the nitrogen atom to form a group selected from the group consisting of

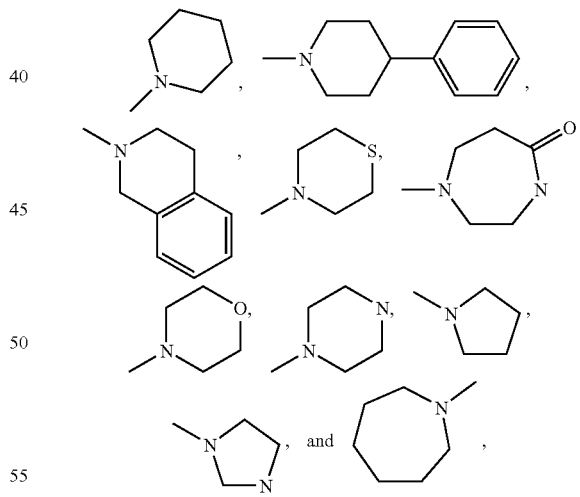

each of which is optionally substituted with a group selected from the group consisting of halogen, amino, $C_1$-$C_8$ alkyl, $C_1$-$C_8$ haloalkyl, $C_1$-$C_8$ thioalkyl, —$C_1$-$C_8$ alkylamino, phenyl, $C_1$-$C_8$ alkylsubstituted phenyl, $C_4$-$C_8$ heterocycle or —$C_1$-$C_4$ alkylheterocycle.

Preferred $R^3$ and $R^{3'}$ Groups

A preferred $R^3$ is hydrogen. A preferred $R^{3'}$ group is selected from hydrogen, methyl, ethyl, propyl, isopropyl, butyl, isobutyl, phenyl and benzyl.

Preferred R⁴ Groups

A preferred $R^4$ group is selected from the group consisting of hydrogen, halo, $C_1$-$C_5$ alkyl, $C_1$-$C_5$ haloalkyl, $C_1$-$C_5$ alkoxy, —$C_1$-$C_5$ alkylamino, —N($C_1$-$C_5$ alkyl)$_2$, —NHC$_1$-$C_5$ alkyl, —$C_1$-$C_5$ alkyl N($C_1$-$C_5$ alkyl)$_2$, —$C_1$-$C_5$ alkyl-NHC$_1$-$C_5$ alkyl, phenyl, —$C_1$-$C_5$ alkylphenyl, —$C_1$-$C_5$ alkylcycloalkyl, and $C_1$-$C_5$ thioalkyl. More preferred is a $R^4$ group selected from the group consisting of hydrogen, methyl, ethyl, isopropyl, chloro, fluoro, trifluoromethyl, methoxy, ethoxy, thiomethyl, phenyl, and benzyl. Most preferred is an $R^4$ group selected from the group consisting of hydrogen, methyl, ethyl, isopropyl, fluoro, chloro, trifluoromethyl, methoxy, ethoxy, propoxy, isopropoxy, and benzyl.

Though the groups $R^4$ and a $R^5$ may exist as multiple substituents on their respective ring substrates, a preferred embodiment of the invention involves compounds wherein each of $R^4$, and $R^5$ are independently singly or doubly substituted on their respective ring substrates.

Preferred R⁵ Groups

A preferred $R^5$ group is selected from the group consisting of hydrogen, halo, $C_1$-$C_5$ alkyl, $C_1$-$C_5$ haloalkyl, $C_1$-$C_5$ alkoxy, —$C_1$-$C_5$ alkylamino, —N($C_1$-$C_5$ alkyl)$_2$, —NHC$_1$-$C_5$ alkyl, —$C_1$-$C_5$ alkylN($C_1$-$C_5$ alkyl)$_2$, —$C_1$-$C_5$ alkyl-NHC$_1$-$C_5$ alkyl, phenyl, —$C_1$-$C_5$ alkylphenyl, —$C_1$-$C_5$ alkylcycloalkyl, and $C_1$-$C_5$ thioalkyl. More preferred is an $R^5$ group selected from the group consisting of hydrogen, methyl, ethyl, isopropyl, chloro, fluoro, trifluoromethyl, methoxy, ethoxy, thiomethyl, phenyl, and benzyl. A most preferred $R^5$ group is selected from the group consisting of hydrogen, methyl, ethyl, isopopropyl, fluoro, chloro, trifluoromethyl, methoxy, ethoxy, trifluoromethoxy, and benzyl.

Preferred R⁶ and R⁷ Groups

Preferred are $R^6$ and $R^7$ groups independently selected from the group consisting of hydrogen, methyl, ethyl, propyl, pentyl, isopropyl, phenyl and benzyl.

Also preferred are compounds of formula I wherein $R^6$ and $R^7$ may independently combine with each other to form a 5, 6, or 7-membered nitrogen containing heterocycle which nitrogen containing heterocycle may optionally have substituents selected from the group consisting of oxo, amino, $C_1$-$C_8$ alkyl, $C_2$-$C_8$ alkenyl, $C_2$-$C_8$ alkynyl, phenyl, —$C_1$-$C_8$ alkylaryl, —C(O)$C_1$-$C_8$ alkyl, —CO(O)$C_1$-$C_8$ alkyl, hydroxy, $C_1$-$C_8$ alkoxy, halo, and haloalkyl.

Preferred A-Ring

A preferred A-ring is a phenyl ring or a pyridine ring.

Preferred B-Ring

A preferred B-ring is a phenyl ring, a pyrazine ring, a pyrimidine ring or a pyridine ring. Most preferred B ring is a phenyl, pyrazine or pyridine ring.

Preferred Values for y, z, v, m and n

A preferred value of y is 0, 1 or 2. More preferred is a compound where y is 0 or 1.

A preferred value of z is 0, 1 or 2. More preferred is a compound where z is 0 or 1.

A preferred value for v is 1, or 2.

A preferred value of m is 1, or 2.

A preferred value for n is 1, 2 or 3.

A preferred compound according to the present invention is a compound selected from the group consisting of:

6-{4-[(3-Methyl-butylamino)-methyl]-phenoxy}-nicotinamidic acid ethyl ester

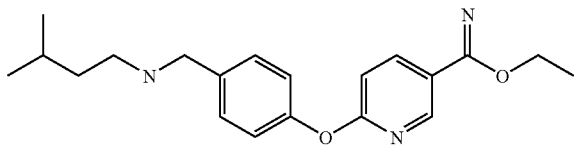

N-Hydroxy-6-{4-[(3-methyl-butylamino)-methyl]-phenoxy}-nicotinamidine

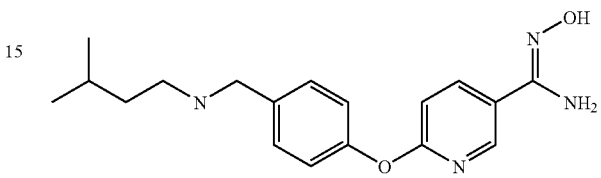

6-{4-[(3-Methyl-butylamino)-methyl]-phenoxy}-nicotinamidine

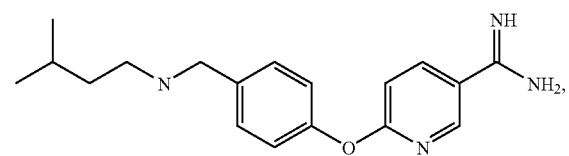

{4-[5-(4,5-Dihydro-1H-imidazol-2-yl)-pyridin-2-yloxy]-benzyl}-(3-methyl-butyl)-amine

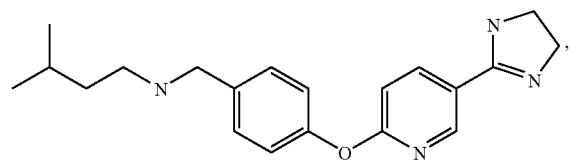

{4-[5-(4,5-Dihydro-1H-imidazol-2-yl)-pyridin-2-yloxy]-benzyl}-(2-thiophen-2yl-ethyl)amine

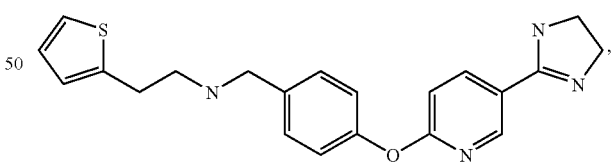

(3-Methyl-butyl)-{4-[5-(1,4,5,6-tetrahydro-2-yl)-pyridin-2-yloxy]-benzyl}-amine

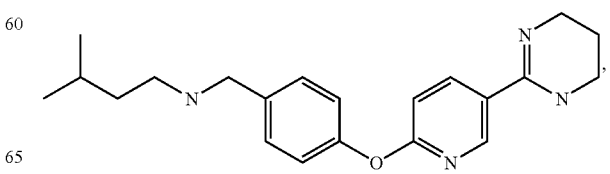

N-Cyano-6-{4-[(3-methyl-butylamino)-methyl]-phenoxy}-nicotinamidine

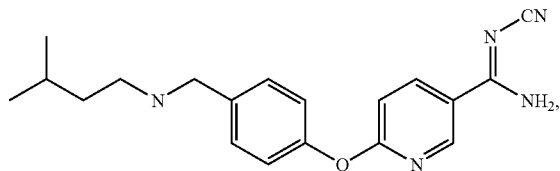

(3-Methyl-butyl)-{4-[5-(2H-tetrazol-5-yl)-pyridin-2-yloxy]-benzyl}-amine

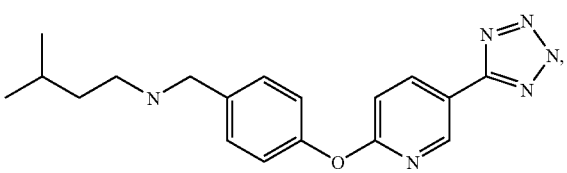

{4-[5-(1H-Imidazol-2-yl)-pyridin-2-yloxy]-benzyl}-(3-methyl-butyl)-amine

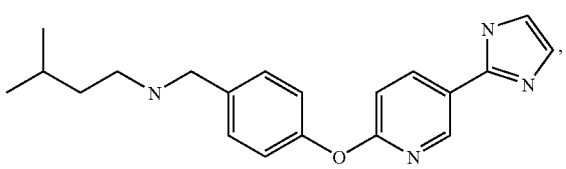

N-(2,2-Dimethoxy-ethyl)-6-{4-[(3-methyl-butylamino)-methyl]-phenoxy}-nicotinamidine

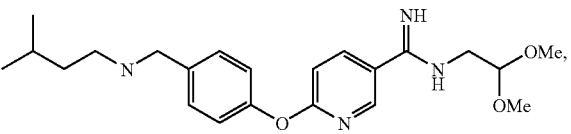

and a pharmaceutically acceptable salt, solvate, enantiomer, diastereomer and diastereomeric mixture thereof.

Preparing the Compound of the Invention

Compounds of formula I may be prepared as described in the following Schemes and Examples. The compounds employed as initial starting materials in the synthesis of compounds of the invention are well known and, to the extent not commercially available, are readily synthesized using specific references provided, or by standard procedures commonly employed by those of ordinary skill in the art and/or are found in general reference texts.

More particularly, the compounds of the invention are produced in accordance with schemes 1 through 9 that are described in detail below, or analogous methods thereto known to one of skill in the art. These reactions are often carried out following known procedures, methods, or analogous methods thereof. Examples of such known procedures and methods include those described in general reference texts such as Comprehensive Organic Transformations, VCH Publishers Inc, 1989; Compendium of Organic Synthetic Methods, Volumes 1-10, 1974-2002, Wiley Interscience; Advanced Organic Chemistry, Reactions Mechanisms, and Structure, 5$^{th}$ Edition, Michael B. Smith and Jerry March, Wiley Interscience, 2001; Advanced Organic Chemistry, 4$^{th}$ Edition, Part B, Reactions and Synthesis, Francis A. Carey and Richard J. Sundberg, Kluwer Academic/Plenum Publishers, 2000, etc., and references cited therein.

In a typical protocol, an optionally substituted benzonitrile or pyridine carboxamide or analog thereof, having a leaving group such as halogen, preferably fluoro, bromo, chloro, or a alkylsulfonyl or other suitable leaving group is reacted with a nucleophilic group such as for example, hydroxy phenyl carboxaldehyde or analog or derivative thereof to form a nitrile intermediate which is then elaborated using known reactions to afford the desired compound of formula I. For example according to Scheme 1,

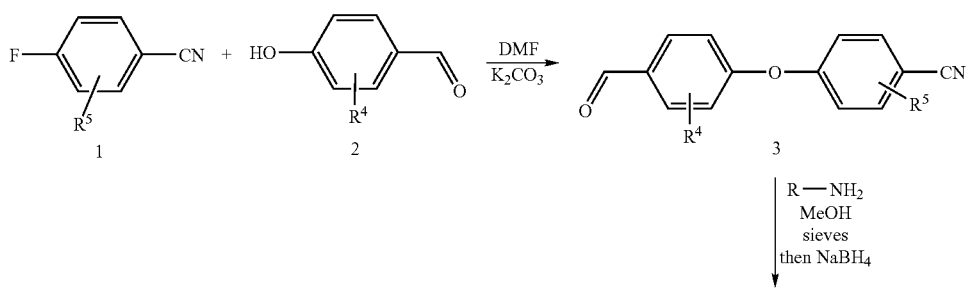

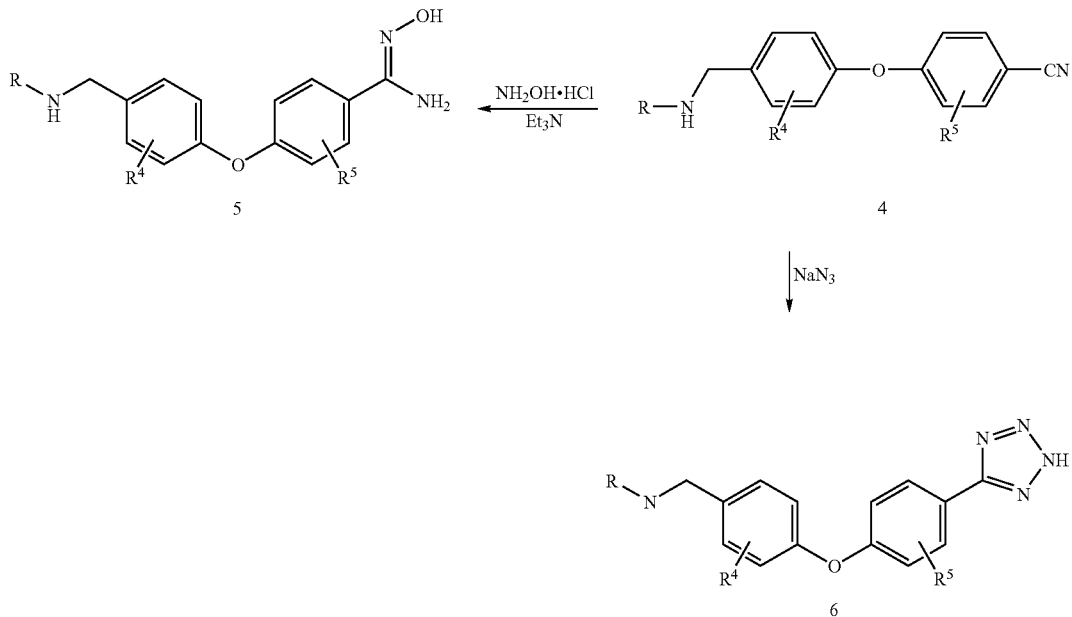

optionally substituted 4-fluorobenzonitrile is reacted with an optionally substituted 4-hydroxybenzaldehyde to afford the ether compound 3, under basic conditions. Basic conditions include the use of bases selected from inorganic and organic bases. Examples of useful inorganic bases include but are not limited to potassium carbonate, sodium hydride, sodium carbonate, sodium hydroxide, potassium hydroxide, calcium carbonate and cesium carbonate. Examples of organic bases include but are not limited to potassium hexamethyl disilazide, n-butyl lithium, Hexamethylphophoroustriamide, (HMPT), and the like. The basic conditions are complemented by the presence of a solvent, preferably an organic solvent. Preferred organic solvents include protic solvents or polar aprotic solvents. Most preferred solvents include dimethylformamide, methanol, dimethylacetamide (DMA), dimethylsulfoxide. A most preferred basic reaction condition involves the use of potassium carbonate in dimethylacetamide at temperatures of about 60 to 100° C.

The reductive amination of compound 3 results in the compound of formula 4. Analogues of compounds 3 and 4 having one or more substituent $R^4$ and $R^5$ groups may be prepared by using appropriately substituted starting materials or by interconversion of substituent functionality. For example an initial substituent $R^4$ and $R^5$ group may be protected and deprotected appropriately to achieve the desired end substituent $R^4$ and/or $R^5$. Alternatively; an initial substituent $R^4$ and/or $R^5$ may be converted by known reactions to other desired $R^4$ and/or $R^5$ substituents. The compound 4 may be reacted with hydroxylamine, preferably as the HCl salt in the presence of a base such as triethylamine and in a suitable solvent such as ethanol to afford the N-hydroxy amidine compound 5. The reaction is preferably performed under reflux conditions. The compound 4 may also be converted to the tetrazole compound (6) by treating a solution of 4 in DMF with sodium azide and ammonium chloride at reflux for about 48 hours or based on satisfactory completion of reaction. The reaction mixture is poured into water and the pH is adjusted to about 3. The product is extracted into ethyl acetate and further purified using processes known to one of skill in the art and as disclosed in the experimental section or analogous methods thereto.

An alternate protocol illustrated in Scheme 2 shows the use of the 6-Chloro-nicotinonitrile as starting material to prepare certain compounds of formula I having the pyridinyl B-ring.

Scheme 2

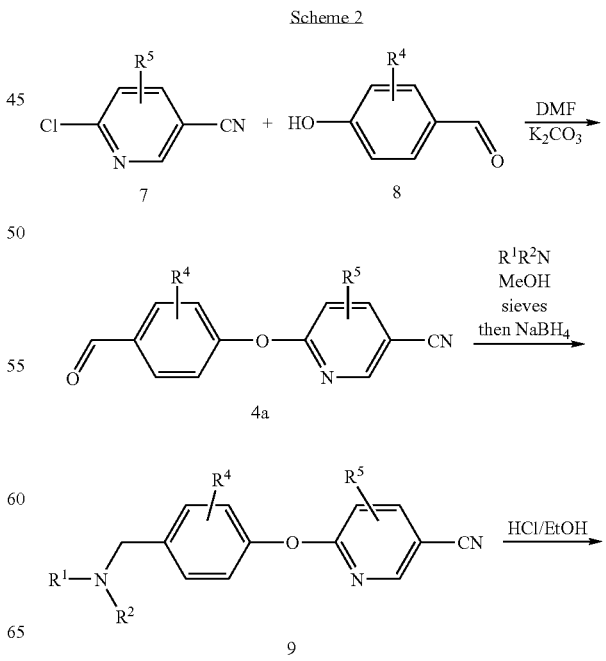

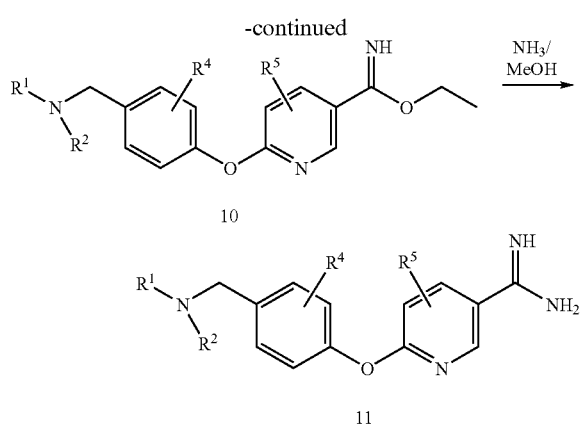

According to scheme 2, the use of nicotino-nitrile compounds having a suitable leaving group affords the nicotino-nitrile ether compound 4a when reacted with an optionally substituted hydroxy-benzaldehyde. The reaction is carried out under basic conditions of reflux using DMF as solvent and potassium carbonate as base. The details of this etherification reaction have been discussed previously and are known or achievable by one of skill in the art without undue experimentation. The ether compound 4a is then reductively aminated with a suitable amine to afford the amino-nitcotinonitrile compound 9. The compound 9 is treated with HCl in EtOH to yield the imidate 10. The compound 10 is then reacted with a solution of ammonia in methanol (preferably about 7M concentration) to afford the amidine compound 11.

Alternatively, the imidate 10 may be converted to other compounds of the invention following procedures known to one of skill in the art or as disclosed herein. For example, reaction of 10 with aminoacetaldehyde dimethylacetal to form the N-dimethylethylamidine compound. The N-dimethylethylamidine compound may in turn be converted to the imidazolyl compound by reaction with ethylene diamine at room temperature over a period of about 24 hours. Alternatively, the imidate 10 may be reacted with 1,3-diaminopropane or 1,4-diaminobutane to form the corresponding tetrahydropyrimidine or diazepine compounds respectively.

Compounds of formula I having varying alkyl chain lengths on the amino side chain may be prepared in one instance by carbonyl elongation reactions. An example is a modified Wittig type reaction as shown in Scheme 3.

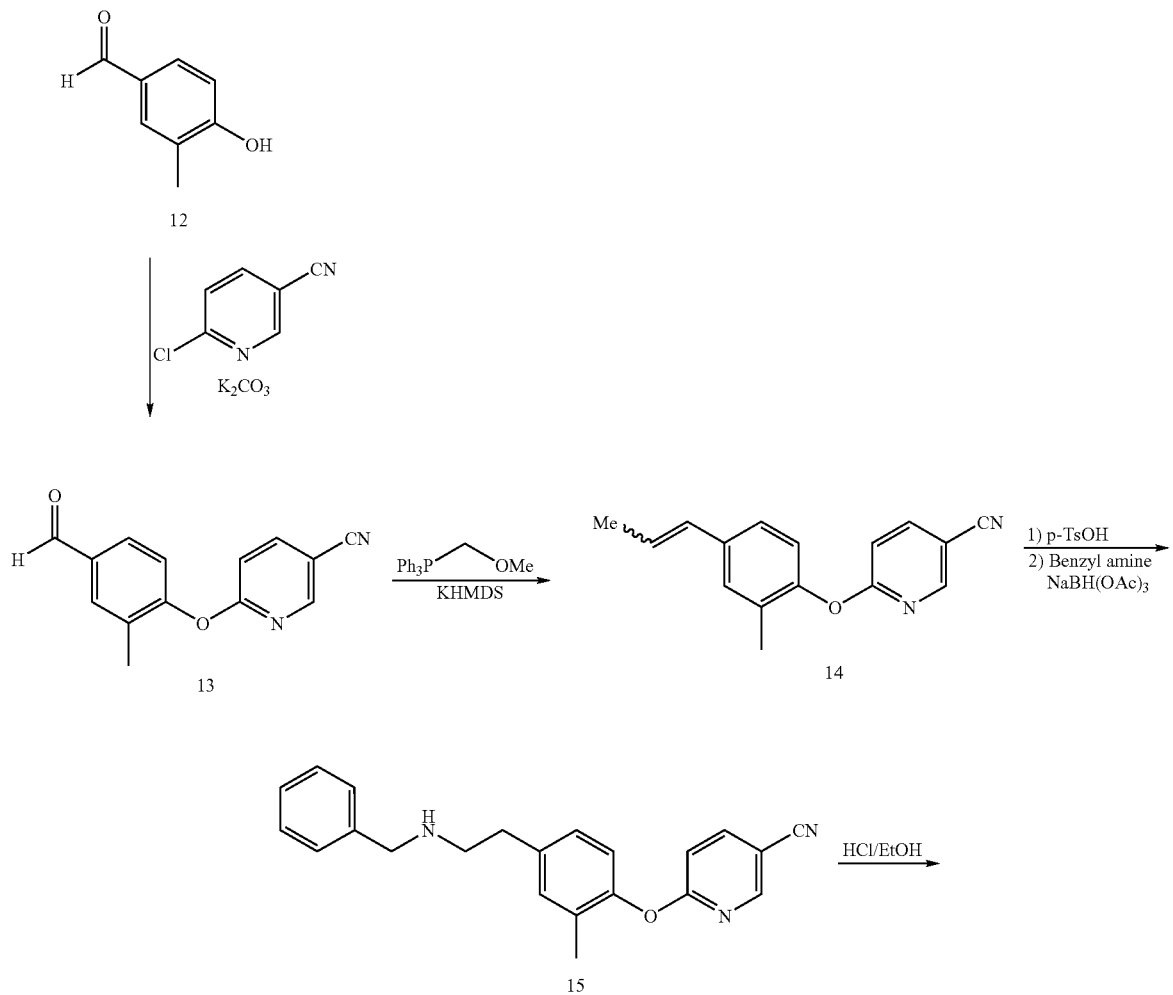

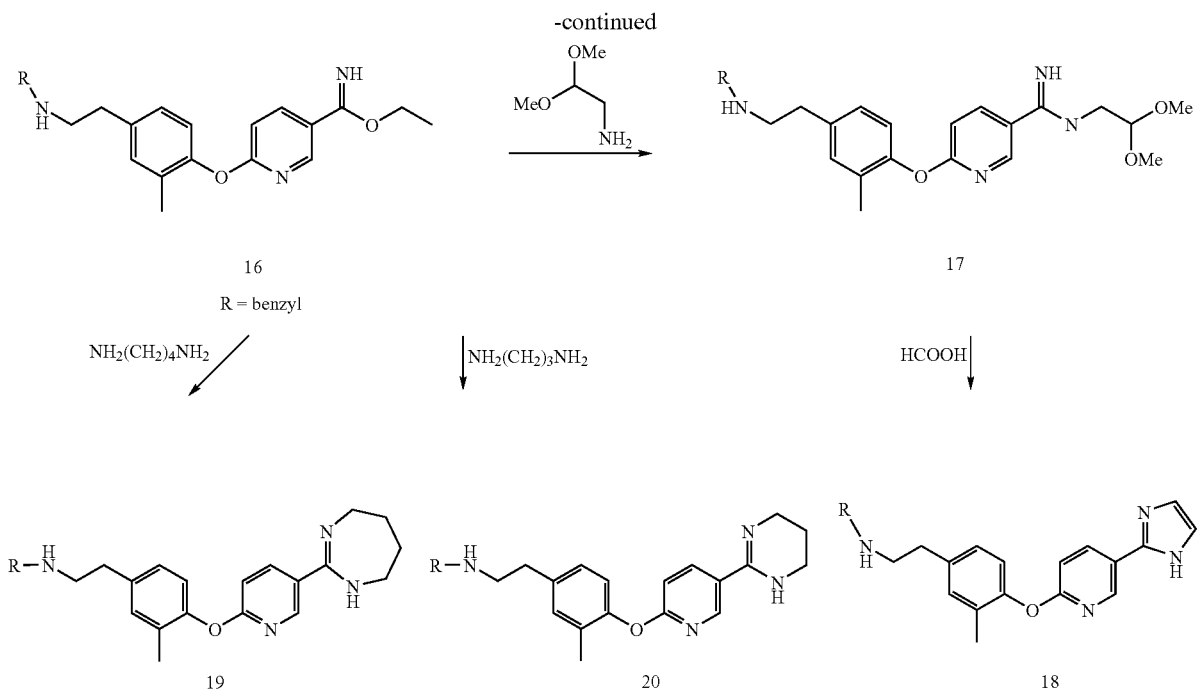

The protocol of Scheme 4 and known variations thereof allow manipulation of the amino side chain for chain length and/or substituents. Under this protocol, optionally substituted 4-hydroxy benzaldehyde e.g. compound 12 is reacted with optionally substituted benzonitrile having a suitable leaving group such as halo, alkylsulfonyl, and the like. The coupled product 13 or analog thereof, is then subjected to a carbonyl elongation reaction such as, for example, the Wittig reaction and variations thereof (see Organophosporus agents in *Organic Synthesis*, J. I. G. Cadogan, Ed., Academic Press London (1979); see also, J. March, *Advanced Organic Chemistry*, 3$^{rd}$ Edition, Wiley Interscience, New York N.Y., (1995). In the example shown, the coupled product 13 is reacted with methoxymethyl triphenylphosphine (available from Aldrich chemical Company, Milwaukee, USA) at the aldehydic functional group using a strong base such as, for example, n-butyllithium, sec-butyllithium and the like, to generate the incipient carbanion. The resulting vinymethyl ether 14 is hydrolyzed using a strong acid such as, for example, p-toluenesulfonic acid, HCl or sulfuric acid to generate the new aldehyde intermediate. The new aldehyde intermediate is then reacted with a suitable amine followed by reduction to afford the reductive amination product 15. Details of each step in the schemes disclosed herein may be found in reference organic synthesis texts or are known to one of skill in the art. Some reactions such as the formation of the ylide specie for the Wittig and related reactions perform better at reduced temperatures ranging from about −10° C. to about −70° C. Other reactions perform better at elevated temperatures ranging from about 30° C. to about 150° C., and yet other reactions perform better at ambient temperature ranging from about 15° C. to about 30° C. The resulting nicotino-nitrile compound 15 may be converted to the compounds of the invention following procedures known to one of skill in the art or as disclosed herein. For example, reaction of 15 with an ethanol solution of HCl affords the imidate 16, a compound of the invention. The ethoxy group of 16 may be displaced by reaction with aminoacetaldehyde dimethylacetal to form the N-dimethylethylamidine compound 17. The dimethyl ethylamidine compound 17 may in turn be converted to the imidazolyl compound 18 by reaction with ethylene diamine at room temperature over a period of about 24 hours. Alternatively, the imidate 16 may be reacted with 1,3-diaminopropane or 1,4-diaminobutane to form the corresponding tetrahydropyrimidine or diazepine compounds 19 and 20 respectively.

Compounds of formula I wherein the B ring is pyrazinyl, for example, may be prepared according to scheme 4 below:

Scheme 4

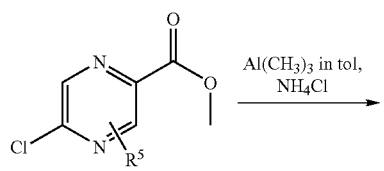

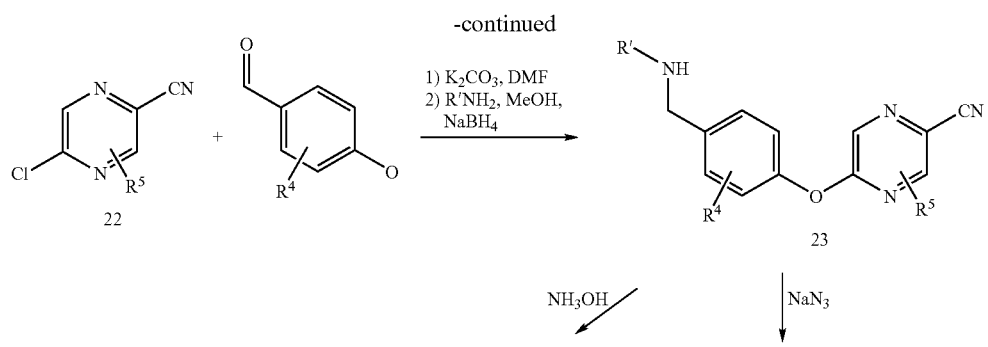

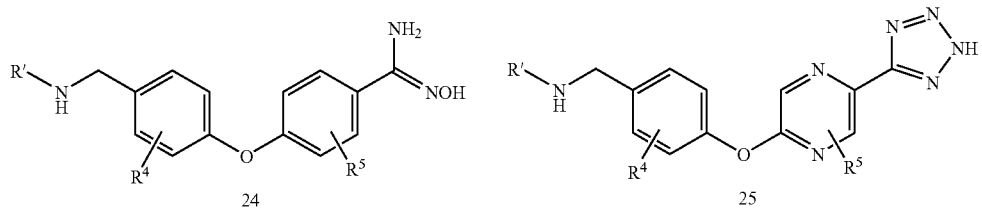

According to Scheme 4, an optionally substituted cyanopyrazinyl group having a suitable leaving group is prepared by reaction of an optionally substituted 5-chloropyrazinyl 2-carboxymethylester 21 with dimethylamine aluminum amide complex. The complex may be or purchased or formed by reaction of one equivalent of ammonium chloride with trimethyl aluminum using procedures known to one of skill in the art. The nitrile 22 is then reacted with an optionally substituted hydroxybenzaldehyde to afford the coupled product 23. The coupled product 23 may be converted to various compounds of the invention using procedures disclosed herein or known to one of skill in the art. For example, scheme 4 shows the reaction of coupled product 23 with hydroxylamine to afford the hydroxy amidine compound 24. Scheme 4 also shows the reaction of coupled product 23 with sodium azide to form the tetrazole compound 25 both of which are examples of compounds of formula I.

Compounds wherein R¹ and/or R² is independently a cyclic group, i.e. saturated or unsaturated monocyclic carbocycle or heterocycle may be prepared as shown below in Scheme 5.

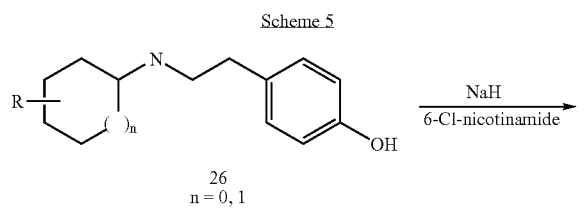

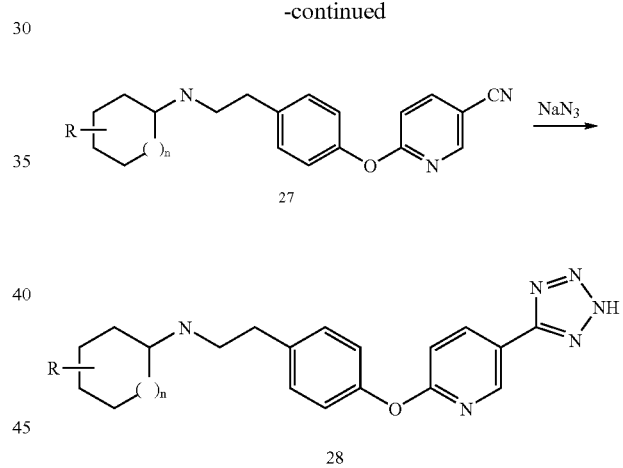

According to Scheme 5 the A ring component compound 26 having a pre-installed amino side chain is reacted with a source of the B-ring component such as the halogeno-nicotinonitrile (e.g. 6-chloronicotino nitrile) to form the compound 27. The amino group 26 is prepared by reductive amination of 4-hydroxy phenacetaldehyde and the respective amine. The phenacetaldehyde may itself be purchased or prepared from the corresponding benzaldehyde by carbonyl elongation reactions i.e. by the Wittig or modified Wittig reaction as discussed previously.

Scheme 5 shows specifically the conversion of the intermediate compound 27 to the tetrazole compound 28. The formation of the tetrazole compound has been described previously and in the examples infra. One of skill in the art is aware that the intermediate 27 may be converted to any of the many compounds of the invention as shown herein or using procedures known to one of skill in the art.

An alternative protocol for preparing certain compounds of the invention is shown in Scheme 6.

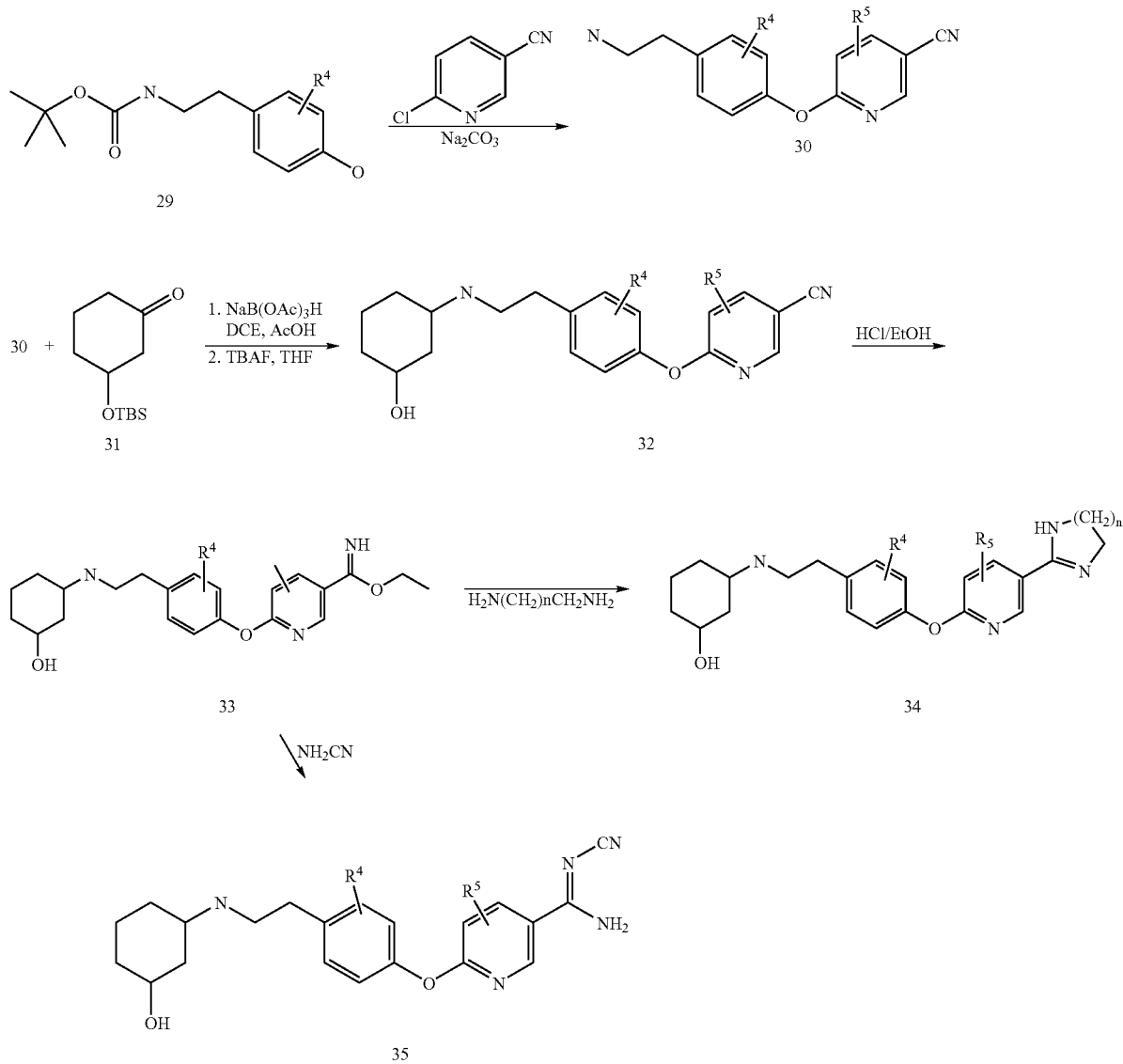

Scheme 6

As shown in Scheme 6, an amine substrate having the A-ring, e.g., 4-hydroxyphenethyl amine is protected at the amino group using, for example, the Boc-protecting group or other typical amino protecting groups. The Boc-protected amine 29 is coupled to the B-ring component, e.g., nicotinonitrile or derivative thereof as discussed previously to afford the coupled compound 30. The coupled product 30 is then de-protected and reductively aminated with an aldehyde or ketone having the desired $R^1$ and/or $R^2$ group per the structure and scope of formula I. For illustration only, the use of a cyclic ketone is shown. As shown, tertiary butyl dimethyl silyl (TB-DMS) protected 3-hydroxycyclohexanone 31 is reacted with the amine 30 having the A and B rings already in place, to form the desired intermediate nitrile compound 32 upon desilylation.

The preferred reaction conditions for each step of the reactions or schemes disclosed herein are known to one of skill in the art or ascertainable with minimal experimentation by one of skill in the art following all the teachings disclosed and/or referenced herein. Substituents such as "R, R' $R^4$ and $R^5$" groups used in the schemes are for illustration purposes only and are not intended to limit the scope of the number and/or type of substituents. One of skill in the art is aware of substituent-types and multiplicities thereof that are suitable and/or possible for a particular position of the compounds drawn for illustrative purposes. Thus, the use of a particular substrate or compound for illustration purposes does not imply a limitation with respect to the workability of the particular scheme for other compounds within the ambit of the invention unless so stated.

Certain compounds of the invention may also be accessed by protocols such as Scheme 7

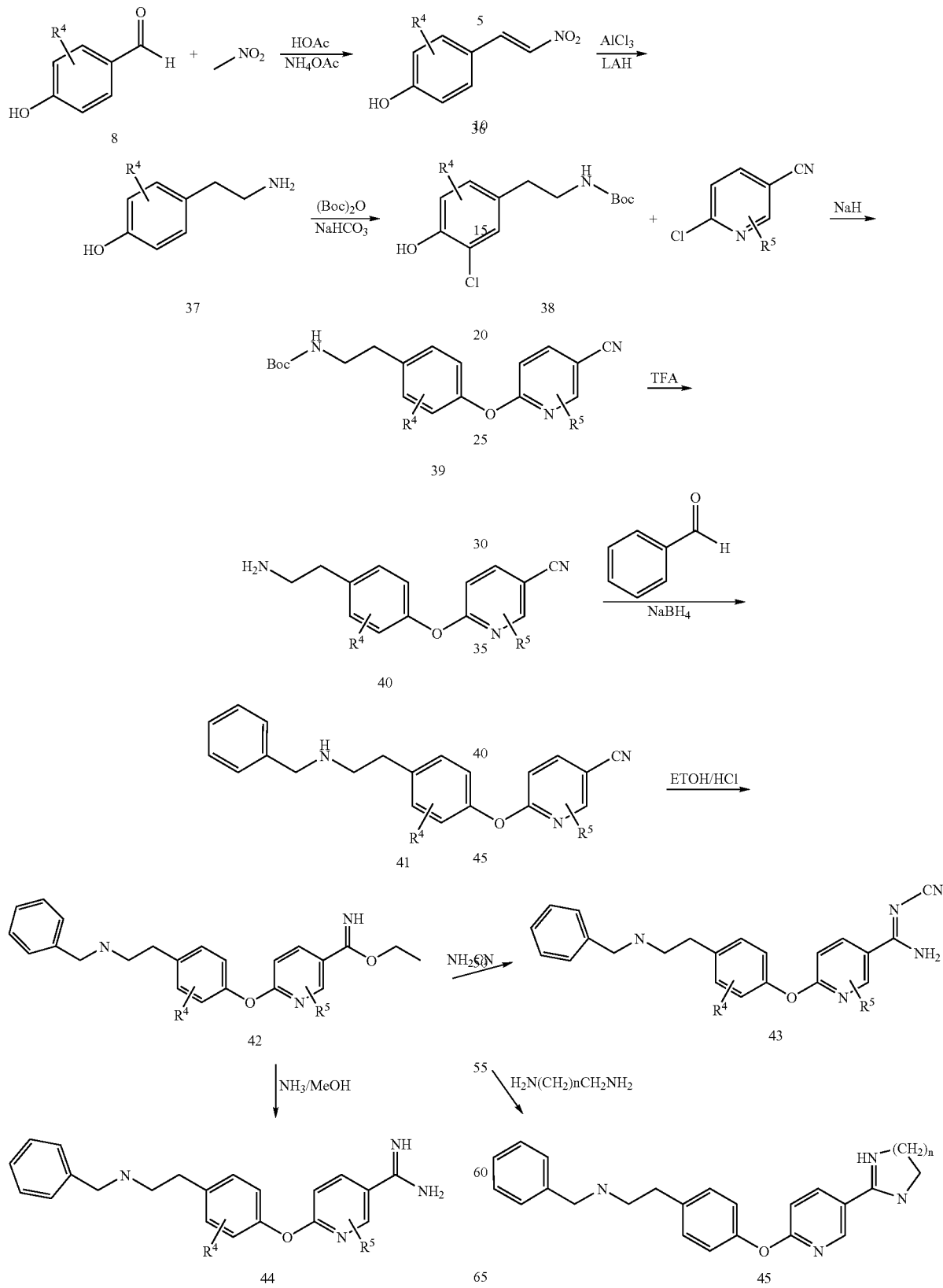

For example, compounds of formula I having "y" groups other than hydrogen or having n (formula I) greater 1, may be more readily accessed by a Michael addition of nitromenthane on an aldehyde e.g., aldehyde 8, having the desired A ring substituents. The resulting product (nitroalkene) is reduced and optionally protected for example by use of a Boc-group. The protected amino compound (e.g. 38) is then reacted with appropriately substituted nicotino-nitrile to afford the intermediate 39 useful in preparing various compounds of formula I as shown.

For example, the amidine 44 was prepared from imidate 42 using ammonia as the reagent in methanol solvent. The imidazoline and other heterocyclic amines were respectively obtained from 42 by using the corresponding alkyldiamines.

Similarly, cyanoamidine 44 is prepared from the imidate 42 by reaction with cyanamide.

Scheme 8 shows the formation of regioisomeric intermediate compounds of the invention and their separation to afford different compounds of the invention.

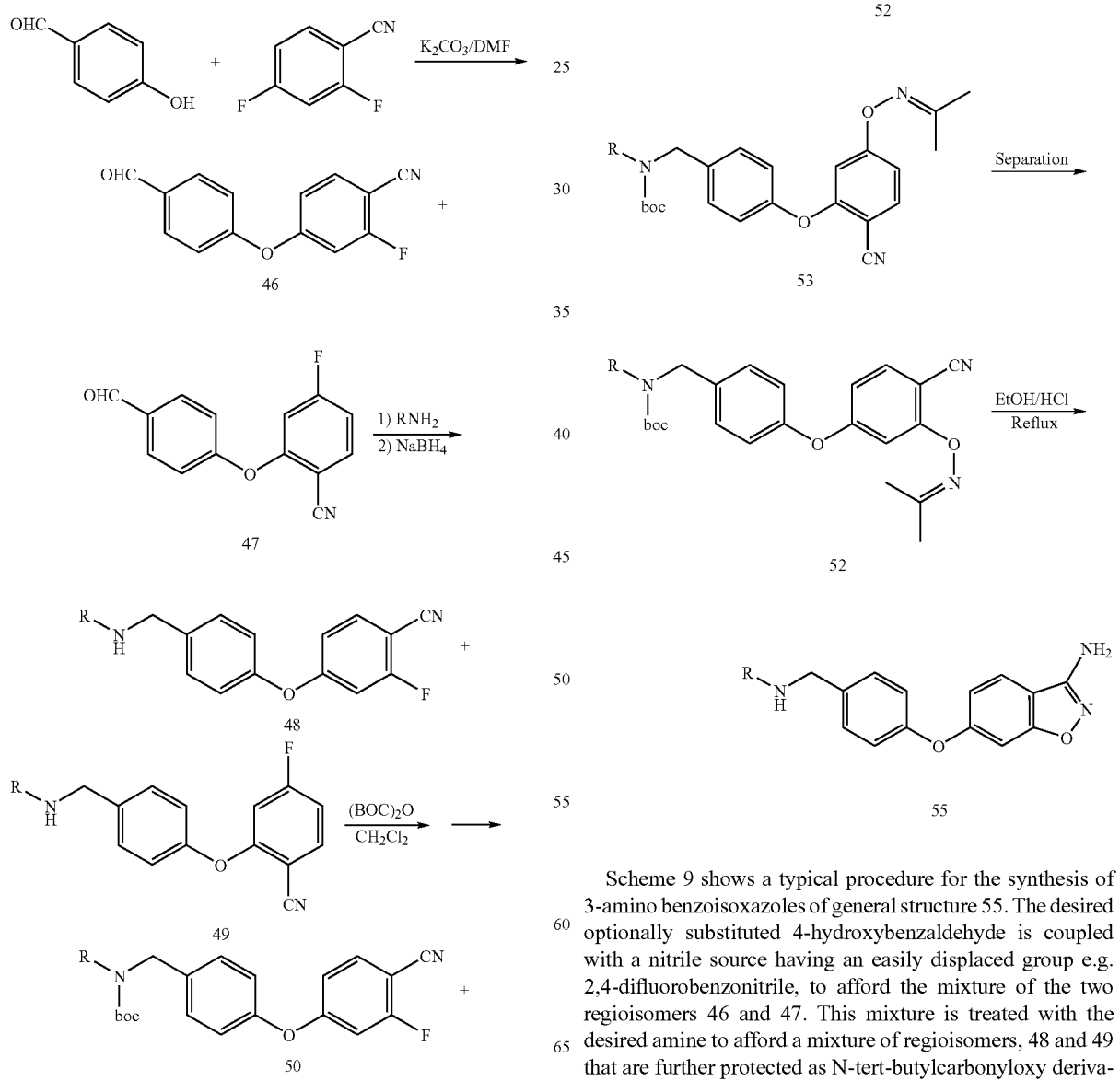

Scheme 9 shows a typical procedure for the synthesis of 3-amino benzoisoxazoles of general structure 55. The desired optionally substituted 4-hydroxybenzaldehyde is coupled with a nitrile source having an easily displaced group e.g. 2,4-difluorobenzonitrile, to afford the mixture of the two regioisomers 46 and 47. This mixture is treated with the desired amine to afford a mixture of regioisomers, 48 and 49 that are further protected as N-tert-butylcarbonyloxy derivatives 50 and 51.

The remaining fluorine atom is displaced by reaction with the oxime of acetone. The mixture of 52 and 53 is easily separated to afford the individual regioisomers, or carried forward to the next step, or the separation is performed later. Regioisomer 52 is then treated with formic acid to afford the desired 3-amino benzoisoxazole 55.

Method of Using the Invention

As noted above, the compounds of the present invention are useful in blocking the effect of agonists at mu, kappa, and/or delta opioid receptors. As such, the present invention also provides a method for blocking a mu, kappa, delta receptor or receptor combination (heterodimer) thereof in a mammal comprising administering to said mammal a receptor blocking dose of a compound of formula I.

The term "receptor blocking dose", as used herein, means an amount of a compound of formula I necessary to block a mu, kappa, or delta receptor or receptor combination (heterodimer) thereof following administration to a mammal requiring blocking of a mu, kappa, or delta receptor or receptor combination (heterodimer) thereof.

The compounds of formula I or combinations thereof, are effective over a wide dosage range. For example, dosages per day will normally fall within the range of about 0.05 to about 250 mg/kg of body weight. In the treatment of adult humans, the range of about 0.5 to about 100 mg/kg, in single or divided doses, is preferred. However, it will be understood that the amount of the compound actually administered will be determined by a physician in light of the relevant circumstances, including the condition to be treated, the choice of compound to be administered, the age, weight, and response of the individual patient, the severity of the patient's symptoms, and the chosen route of administration. Therefore, the above dosage ranges are not intended to limit the scope of the invention in any way. The compounds may be administered by a variety of routes such as the oral, transdermal, subcutaneous, intranasal, intramuscular and intravenous routes.

A variety of physiologic functions have been shown to be subject to or influenced by mu, kappa, or delta receptors or receptor combination (heterodimers) in the brain. As such, the compounds of the present invention are believed to have the ability to treat disorders associated with these receptors or combinations thereof, such as eating disorders, opioid overdose, depression, smoking, alcoholism, sexual dysfunction, shock, stroke, spinal damage and head trauma. As such, the present invention also provides methods of treating the above disorders by blocking the effect of agonists at a mu, kappa, delta receptors or receptor combinations (heterodimer) thereof. Compounds of the present invention have been found to display good activity in an opioid receptor binding assay which measures the ability of the compounds to block the mu, kappa, delta or receptors combination (heterodimer) thereof.

GTP-γ-S Binding Assay

An SPA-based GTP-γ-S assay format was developed based on previous opioid (Emmerson et al., J. Pharm Exp Ther 278, 1121, 1996; Horng et al., Society for Neuroscience Abstracts, 434.6, 2000) and muscarinic (DeLapp et al., JPET 289, 946, 1999) assay formats. Membranes were re-suspended in 20 mM HEPES, 100 mM NaCl, 5 mM $MgCl_2$, 1 mM DTT, and 1 mM EDTA. Fifty (50) mL of GTP-γ-[35S], compound, membrane suspension (20 microgram/well), and wheat germ agglutinin coated SPA beads (1 mg/well) were added to clear bottom 96 well assay plates. GDP (200 mM) was added to the membrane solution prior to addition to the assay plates. Plates were sealed and incubated for four hours at room temperature then placed in a refrigerator overnight to allow the beads to settle. Signal stability at 4° C. was determined to be >60 hours. Plates were warmed to room temperature and counted in a Wallac Microbeta scintillation counter. Results obtained for a representative sample of compounds of the invention are shown in table 1 below.

TABLE 1

| Example # | In Vitro Ki | | |
|---|---|---|---|
| | Mu (nM) | Kappa (nM) | Delta (nM) |
| 2 | 43.43 | 117.09 | 269.06 |
| 3 | 46.14 | 134.05 | 484.63 |
| 4 | 9.50 | 34.10 | 119.62 |
| 5 | 16.38 | 32.76 | 369.72 |
| 8 | 7.83 | 43.16 | 177.85 |
| 10 | 5.77 | 40.08 | 214.01 |
| 11 | 5.81 | 47.49 | 81.14 |

For antagonist assays, specific agonists were added at the following concentrations: (MOR) DAMGO 1 micromolar, (DOR) DPDPE 30 nM, (KOR) U69593 300 nM. Kb's were determined by Cheng-Prusoff equation (see Cheng and Prusoff, Biochem. Pharmacol. 22, 3099, 1973).

Formulation

A compound of the invention is preferably presented in the form of a pharmaceutical formulation comprising a pharmaceutically acceptable carrier, diluent or excipient and a compound of the invention. Such compositions will contain from about 0.1 percent by weight to about 90.0 percent by weight of the compound of the invention (Active Ingredient). As such, the present invention also provides pharmaceutical formulations comprising a compound of the invention and a pharmaceutically acceptable carrier, diluent or excipient thereof.

In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material that acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), and soft and hard gelatin capsules.

Examples of suitable carriers, excipients, and diluents include lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, and mineral oil. The formulations may also include wetting agents, emulsifying and suspending agents, preserving agents, sweetening agents or flavoring agents. The formulations of the invention may be formulated so as to provide quick, sustained, or delayed release of the active ingredient after administration to the patient by employing procedures well known in the art.

For oral administration, the Active Ingredient, a compound of this invention, may be admixed with carriers and diluents and molded into tablets or enclosed in gelatin capsules.

The compositions are preferably formulated in a unit dosage form, each dosage containing from about 1 to about 500 mg, more usually about 5 to about 300 mg, of the Active Ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In order to more fully illustrate the operation of this invention, the following formulation examples are provided. The examples are illustrative only, and are not intended to limit the scope of the invention. The formulations may employ as Active Ingredient any of the compounds of the present invention.

Formulation 1

Hard gelatin capsules are prepared using the following ingredients:

| Compound | Amount per capsule (mg) | Concentration by weight (%) |
| --- | --- | --- |
| Active Ingredient | 250 | 55 |
| Starch dried | 200 | 43 |
| Magnesium stearate | 10 | 2 |

The above ingredients are mixed and filled into hard gelatin capsules in 460 mg quantities.

Formulation 2

Capsules each containing 20 mg of medicament are made as follows:

| Compound | Amount per capsule (mg) | Concentration by weight (%) |
| --- | --- | --- |
| Active Ingredient | 20 | 10 |
| Starch | 89 | 44.5 |
| Microcrystalline cellulose | 89 | 44.5 |
| Magnesium stearate | 2 | 1 |

The active ingredient, cellulose, starch and magnesium stearate are blended, passed through a No. 45 mesh U.S. sieve and filled into a hard gelatin capsule.

Formulation 3

Capsules each containing 100 mg of active ingredient are made as follows:

| Compound | Amount per capsule (mg) | Concentration by weight (%) |
| --- | --- | --- |
| Active Ingredient | 100 | 30 |
| Polyoxyethylene Sorbitan monooleate | 50 mcg | 0.02 |
| Starch powder | 250 | 69.98 |

The above ingredients are thoroughly mixed and placed in an empty gelatin capsule.

Formulation 4

Tablets each containing 10 mg of active ingredient are prepared as follows:

| Compound | Amount per capsule (mg) | Concentration by weight (%) |
| --- | --- | --- |
| Active Ingredient | 10 | 10 |
| Starch | 45 | 45 |
| Microcrystalline cellulose | 35 | 35 |
| Polyvinylpyrrolidone (as 10% solution in water) | 4 | 4 |
| Sodium carboxymethyl starch | 4.5 | 4.5 |
| Magnesium stearate | 0.5 | 0.5 |
| talc | 1 | 1 |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granule so produced is dried at 50-60° C. and passed through a No. 18 mesh U.S. sieve. The sodium carboxymethyl starch, magnesium stearate and talc, previously passed through a No. 60 mesh U.S. sieve, are then added to the granules, which after mixing, is compressed on a tablet machine to yield a tablet weighing 100 mg.

Formulation 5

A tablet formula may be prepared using the ingredients below:

| Compound | Amount per capsule (mg) | Percent by weight (%) |
| --- | --- | --- |
| Active Ingredient | 250 | 38 |
| Cellulose microcrystalline | 400 | 60 |
| Silicon dioxide fumed | 10 | 1.5 |
| Stearic acid | 5 | 0.5 |

The components are blended and compressed to form tablets each weighing 665 mg.

Formulation 6

Suspensions each containing 5 mg of medicament per 5 ml dose are made as follows:

| Compound | Amount per 5 mL suspension (ml) |
| --- | --- |
| Active Ingredient | 5 |
| Sodium carboxymethyl cellulose | 50 |
| Syrup | 1.25 |
| Benzoic acid solution | 0.10 |
| Flavor | q.v. |
| Color | q.v. |
| Water | q.s. to 5 mL |

The medicament is passed through a No. 45 mesh U.S. sieve and mixed with the sodium carboxymethylcellulose and syrup to form a smooth paste. The benzoic acid solution, flavor and color is diluted with some of the water and added to the paste with stirring. Sufficient water is then added to produce the required volume.

Formulation 7

An aerosol solution is prepared containing the following components:

| Compound | Concentration by weight (percent) |
|---|---|
| Active Ingredient | 0.25 |
| Ethanol | 29.75 |
| Propellant 22 (chlorodifluoromethane) | 70.0 |

The active compound is mixed with ethanol and the mixture added to a portion of the Propellant 22, cooled to –30° C. and transferred to a filling device. The required amount is then fed to a stainless steel container and diluted further with the remaining amount of propellant. The valve units are then fitted to the container.

EXAMPLES

Intermediate 1

Synthesis of 6-(4-Formyl-phenoxy)-nicotino-nitrile

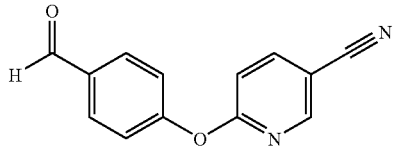

Combine 4-hydroxy-benzaldehyde (1 equiv), 6-chloro-nicotinonitrile (1 equiv), and potassium carbonate (1.5 equiv) in dimethylformamide (0.1 M) and warm to 130° C. with stirring. After 3 h, cool to ambient temperature, dilute reaction mixture with water and extract with ethyl acetate (3×). Wash combined organic extracts with water and brine successively, dry over anhydrous magnesium sulfate, filter, and concentrate. Purify the residue by silica gel chromatography (hexanes:ethyl acetate 6:4) to provide the title compound as a white solid.

55% Yield 1H-NMR (CDCl$_3$, 300.00 MHz): 10.03 (s, 1H); 8.48 (d, J=1.9 Hz, 1H); 7.99 (d, J=8.6 Hz, 2H); 7.98 (s, 1H); 7.33 (d, J=8.6 Hz, 2H); 7.13 (d, J=8.6 Hz, 1H).

Intermediate 2

Synthesis of 6-{4-[(3-Methyl-butylamino)-methyl]-phenoxy}-nicotino-nitrile

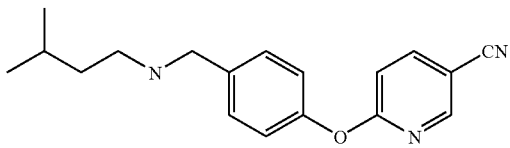

A mixture of intermediate 1 (1 equiv), isoamylamine (1 equiv), 4 Å molecular sieves (1000% weight) in methanol (0.1 M) was stirred overnight under nitrogen atmosphere at room temperature. The following day NaBH$_4$ (5 equiv) was added and the reaction mixture was stirred for 3 hours. The reaction can be monitored by TLC analysis. The reaction mixture was filtered off and the solvent evaporated to yield a residue which was purified by silica gel chromatography using CHCl$_3$:EtOH 7%:NH$_4$OH 0.7 to afford the title compound as a solid.

82% Yield $^1$H NMR (CD$_3$OD, 300 MHz) δ: 8.46 (d, J=2.7, Hz, 1H), 8.09 (dd, J=8.5, 2.1, Hz, 1H), 7.40 (d, J=8.1, Hz, 2H), 7.11 (d, J=8.4, Hz, 2H), 7.13-7.07 (m, 1H), 3.76 (s, 2H), 2.62-2.57 (m, 2H), 1.63-1.58 (m, 1H), 1.47-1.39 (m, 2H), 0.90 (d, J=6.6 Hz, 6H). $^{13}$H NMR (CD$_3$OD, 300 MHz) δ: 165.9, 152.3, 151.9, 142.9, 137.0, 129.8, 121.4, 116.5, 111.8, 104.2, 52.7, 46.9, 38.3, 26.3, 21.9. MS (Electrospray): (M$^+$+1) 296.2

Example 1

Synthesis of 6-{4-[(3-Methyl-butylamino)-methyl]-phenoxy}-nicotinimidic acid ethyl ester

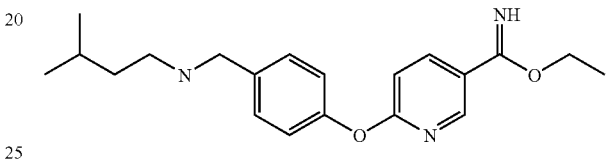

Dry HCl gas was bubbled through a solution of intermediate 2 in absolute EtOH at 0° C. for 4 hours. The reaction can be monitored by HPLC/electrospray MS analysis. The solvent was removed under vacuum. The solid was triturated under Et$_2$O and the white solid was collected by suction filtration.

80% Yield 1H-NMR (CD$_3$OD, 300.00 MHz): 8.78 (s, 1H); 8.45 (dd, J=8.9, 2.4 Hz, 1H); 7.65 (d, J=8.5 Hz, 2H); 7.33-7.27 (m, 3H); 4.70-4.63 (m, 2H); 4.28 (s, 2H); 3.15-3.10 (m, 2H); 1.75-1.60 (m, 4H); 1.00 (d, J=6.3 Hz, 6H). MS (Electrospray): (M$^+$+1) 342.3

Example 2

Synthesis of N-Hydroxy-6-{4-[(3-methyl-butylamino)-methyl]-phenoxy}-nicotinamidine

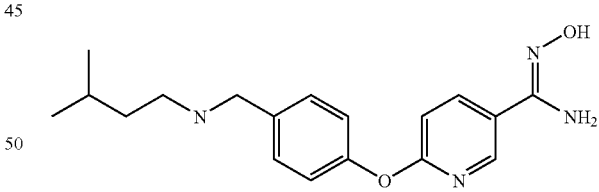

To a solution of intermediate 2 (1 equiv) in ethanol was added hydroxylamine (1.8 equiv) and triethylamine (2.6 equiv). The reaction mixture was heated at reflux for 2 hours. The progress of the reaction was monitored by TLC. The solvent was removed under vacuum and redissolved in CH$_2$Cl$_2$, washed with water, and brine successively. The mixture is dried over anhydrous magnesium sulfate, filtered, and concentrated. It is then purified by silica gel chromatography using CHCl$_3$:EtOH 7%:NH$_4$OH 0.7 to afford the title compound as a white solid.

63% Yield $^1$H NMR (CD$_3$OD, 400 MHz) δ: 8.37 (d, J=2.0, Hz, 1H), 8.04 (dd, J=6.4, 2.0, Hz, 1H), 7.42 (d, J=7.2, Hz, 2H), 7.11 (d, J=8.4, Hz, 2H), 6.96-6.93 (m, 1H), 3.84 (s, 2H), 2.71-2.68 (m, 2H), 1.64-1.59 (m, 1H), 1.47-1.43 (m, 2H), 0.92 (dd, J=6.8, 1.6 Hz, 6H). ¹³H NMR (CD₃OD, 400 MHz) δ: 164.4, 153.5, 151.2, 145.0, 138.1, 134.7, 130.2, 124.7, 121.0, 110.9, 52.5, 46.9, 37.8, 26.5, 22.0. MS (Electrospray): (M⁺+1) 329.1

Example 3

Synthesis of 6-{4-[(3-Methyl-butylamino)-methyl]-phenoxy}-nicotinamidine

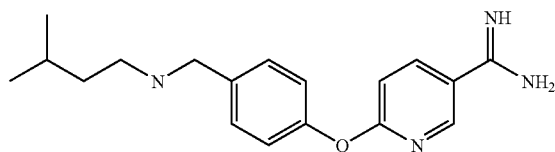

To a solution of the compound of Example 1 (1 equiv) was added ammonia in methanol 7 M. The reaction mixture stirred at room temperature overnight. It was concentrated under reduced pressure and purified by flash chromatography CHCl₃:EtOH 7%:NH₄OH 0.7 to afford the title compound.

63% Yield ¹H NMR (CD₃OD, 400 MHz) δ: 8.51 (s,1H), 8.14 (dd, J=7.6, 0.8, Hz, 1H), 7.41 (d, J=7.6, Hz, 2H), 7.11 (d, J=7.6, Hz, 2H), 7.04 (d, J=8.8, Hz, 1H), 3.76(s, 2H), 2.62-2.59 (m, 2H), 1.63-1.58 (m, 1H), 1.46-1.41 (m, 2H), 0.91 (d, J=6.8, Hz, 6H). ¹³H NMR (CD₃OD, 400 MHz) δ: 166.2, 164.1, 152.8, 147.1, 139.2, 136.8, 129.9, 123.5, 121.2, 111.0, 52.7, 47.0, 38.3, 26.3, 21.8. MS (Electrospray): (M⁺+1) 313.2 HPLC=88% @ 5.60 m (5/95 to 95/5 ACN/(0.1% TFA in water) over 10 minutes, Zorbax SB-Phenyl 4.6 mm×15 cm×5 micron, λ=254 nM.de Example 4

Synthesis of {4-[5-(4,5-Dihydro-1H-imidazol-2-yl)-pyridin-2-yloxy]-benzyl}-(3-methyl-butyl)-amine

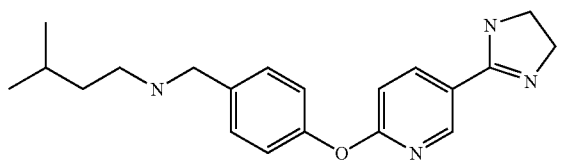

To a solution of the compound of Example 1 (1 equiv) in EtOH was added ethylenediamine. The reaction mixture was stirred at room temperature overnight. It was concentrated under reduced pressure and purified by flash chromatography CHCl₃:EtOH 7%:NH₄OH 0.7 to afford the title compound.

32% Yield ¹H NMR (CD₃OD, 300 MHz) δ: 8.50 (s,1H), 8.15 (d, J=8.4 Hz, 1H), 7.40 (d, J=6.6, Hz, 2H), 7.10 (d, J=6.6, Hz, 2H), 6.97 (dd, J=8.7, 2.1 Hz, 1H), 3.77 (s, 2H), 3.74 (s, 4H), 2.64-2.59 (m, 2H), 1.61-1.59 (m, 1H), 1.47-1.40 (m, 2H), 0.90 (dd, J=6.6, 2.1 Hz, 6H). MS (Electrospray): (M⁺+1) 339.2 HPLC=99% @ 5.60 m (5/95 to 95/5 ACN/(0.1% TFA in water) over 10 minutes, Zorbax SB-Phenyl 4.6 mm×15 cm×5 micron, λ=254 nM.de Example 5

Synthesis of -{4-[5-(4,5-Dihydro-1H-imidazol-2-yl)-pyridin-2-yloxy]-benzyl}-(2-thiophen-2yl-ethyl)amine

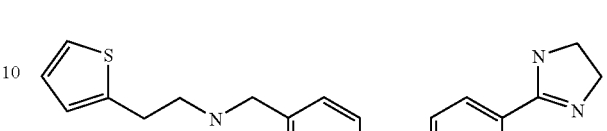

Step 1

6-{4-[(2-Thiophen-2-yl-ethylamino)-methyl]-phenoxy}-nicotinonitrile

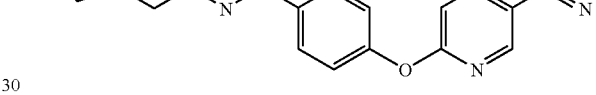

A mixture of intermediate 1 (1 equiv), 2-thiophenethylamine (1 equiv), 4 Å molecular sieves (1000% weight) in methanol (0.1 M) was stirred overnight under nitrogen atmosphere at room temperature. The following day NaBH₄ (5 equiv) was added and the reaction mixture was stirred for 3 hours. The reaction can be monitored by TLC analysis. The reaction mixture was filtered off and the solvent evaporated to yield a residue which was purified by silica gel chromatography using CHCl₃:EtOH 7%:NH₄OH 0.7 to afford the title compound as a solid.

68% Yield 1H-NMR (CDCl₃, 300.00 MHz): 7.91 (dd, J=8.9, 2.4 Hz, 1H); 7.39 (d, J=8.5 Hz, 2H); 7.15 (dd, J=5.3, 1.2 Hz, 1H); 7.09 (d, J=8.5 Hz, 2H); 7.01 (d, J=8.9 Hz, 1H); 6.94 (dd, J=5.3, 3.6 Hz, 1H); 6.85 (d, J=2.8 Hz, 1H); 3.85 (s, 2H); 3.10-3.05 (m, 2H); 2.99-2.94 (m, 2H).

Step 2

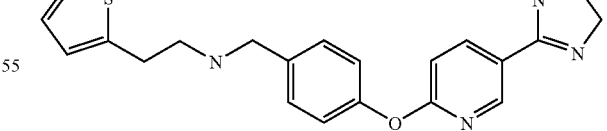

Using a similar method to Example 3 affords the title compound.

Yield 9% 1H-NMR (CD₃OD, 300.00 MHz): 8.52 (d, J=2.4 Hz, 1H); 8.16 (dd, J=8.5, 2.4 Hz, 1H); 7.39 (d, J=8.5 Hz, 2H); 7.20 (d, J=4.8 Hz, 1H); 7.10 (d, J=8.5 Hz, 2H); 6.98 (d, J=8.5 Hz, 1H); 6.93 (dd, J=4.8, 3.6 Hz, 1H); 6.86 (d, J=3.2 Hz, 1H); 3.80 (s, 2H); 3.06 (t, J=7.3 Hz, 2H); 2.89 (t, J=7.3 Hz, 2H). MS (Electrospray): (M⁺+1) 379.1

Example 6

Synthesis of (3-Methyl-butyl)-{4-[5-(4,5,6,7-tetrahydro-1H-[1,3]diazepin-2-yl)-pyridin-2-yloxy]-benzyl}-amine

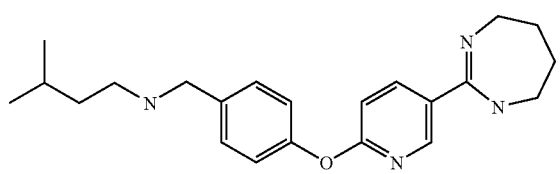

Using a method similar to Example 4 using 1,4-diaminobutane gives the title compound.

33% 1H-NMR (CD$_3$OD, 300.00 MHz): 8.38 (d, J=1.8 Hz, 1H); 8.02 (dt, J=8.7, 1.4 Hz, 1H); 7.42 (d, J=8.5 Hz, 2H); 7.11 (d, J=8.7 Hz, 2H); 6.95 (d, J=8.7 Hz, 1H); 3.78 (s, 2H); 3.55 (s, 4H); 2.65-2.60 (m, 2H); 1.93 (s, 4H); 1.68-1.57 (m, 1H); 1.49-1.42 (m, 2H); 0.93 (d, J=6.7 Hz, 6H). MS (Electrospray): (M$^+$+1) 367.3

Example 7

Synthesis of (3-Methyl-butyl)-{4-[5-(1,4,5,6-tetrahydro-2-yl)-pyridin-2-yloxy]-benzyl}-amine

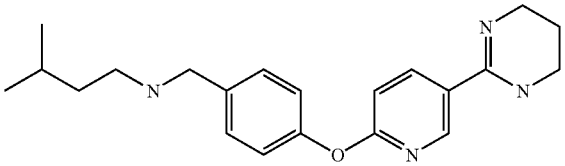

Using a method similar to Example 4 using 1,3-propanediamine gives the title compound.

Yield 49% 1H-NMR (CD$_3$OD, 300.00 MHz): 8.41 (d, J=2.0 Hz, 1H); 8.04 (dd, J=8.7, 2.6 Hz, 1H); 7.42 (d, J=8.5 Hz, 2H); 7.11 (d, J=8.5 Hz, 2H); 6.98 (d, J=8.7 Hz, 1H); 3.78 (s, 2H); 3.48 (t, J=5.7 Hz, 4H); 2.73-2.67 (m, 1H); 2.63 (t, J=7.9 Hz, 2H); 1.95-1.90 (m, 2H); 1.69-1.60 (m, 2H); 1.49-1.42 (m, 2H); 0.93 (d, J=6.5 Hz, 6H). MS (Electrospray): (M$^+$+1) 353.2

Example 8

Synthesis of N-Cyano-6-{4-[(3-methyl-butylamino)-methyl]-phenoxy}-nicotinamidine

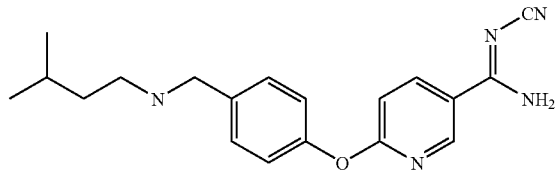

To a solution of the compound of Example 1 (1 equiv) in methanol was added potassium carbonate (1.15 equiv) and cyanamide (1.6 equiv). The reaction mixture stirred at r.t for 48 hours.

The reaction was monitored by TLC. The solvent was removed under vacuum. It was purified by silica gel chromatography using CHCl$_3$:EtOH 7%:NH$_4$OH 0.7 to afford the title compound as a white solid.

35% Yield $^1$H NMR (CD$_3$OD, 300 MHz) δ: 8.64 (d, J=2.7, Hz, 1H), 8.27 (dd, J=8.4, 2.4, Hz, 1H), 7.41 (d, J=8.7, Hz, 2H), 7.11 (d, J=8.4, Hz, 2H), 7.01 (d, J=9.0, Hz, 1H), 3.76 (s, 2H), 2.63-2.58 (m, 2H), 1.63-1.59 (m, 1H), 1.47-1.39 (m, 2H), 0.91 (d, J=6.6, Hz, 6H). $^{13}$H NMR (CD$_3$OD, 400 MHz) δ: 167.9, 166.5, 152.6, 147.6, 139.4, 136.8, 129.9, 123.1, 121.2, 116.2, 110.8, 52.9, 47.2, 38.5, 26.5, 22.1. MS (Electrospray): (M$^+$+1) 338.2 (M$^+$−1) 336.3 HPLC=95% @ 5.92 m (5/95 to 95/5 ACN/(0.1% TFA in water) over 10 minutes, Zorbax SB-Phenyl 4.6 mm×15 cm×5 micron, λ=254 nM.de

Example 9

Synthesis of (3-Methyl-butyl)-{4-[5-(2H-tetrazol-5-yl)-pyridin-2-yloxy]-benzyl}-amine

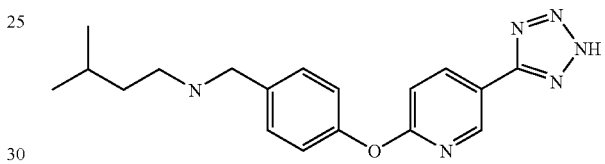

A solution of intermediate 2 (1 equiv.) in DMF was treated with sodium azide (3 equiv.) and ammonium chloride (3 equiv.) and heated at 120° C. for 2 days. The mixture was poured into water and the pH brought to 3 with dilute HCl. The mixture was extracted with ethyl acetate, and the organic phase washed with NaCl(sat) and water. Dry over anhydrous magnesium sulfate, filter, and concentrate. The product was purified by silica gel chromatography using CHCl$_3$:EtOH 7%:NH$_4$OH 0.7 to afford the title compound as a white solid.

55% Yield $^1$H NMR (CD$_3$OD, 300 MHz) δ: 8.76 (s,1H), 8.42 (d, J=8.4 Hz, 1H), 7.54 (d, J=7.5, Hz, 2H), 7.25 (d, J=6.9, Hz, 2H), 7.12 (d, J=8.4, Hz, 1H), 4.2 (s, 2H), 3.12-3.07 (m, 2H), 1.70-1.59 (m, 3H), 0.98 (dd, J=6.6, 1.2 Hz, 6H). MS (Electrospray): (M$^+$+1) 339.2 (M$^+$−1) 337.3 HPLC=86% @ 5.93 m (5/95 to 95/5 ACN/(0.1% TFA in water) over 10 minutes, Zorbax SB-Phenyl 4.6 mm×15 cm×5 micron, λ=254 nM.de

Example 10

Synthesis of {4-[5-(1H-Imidazol-2-yl)-pyridin-2-yloxy]-benzyl}-(3-methyl-butyl)-amine Step 1

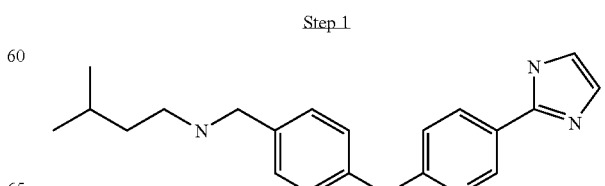

39

N-(2,2-Dimethoxy-ethyl)-6-{4-[(3-methyl-buty-lamino)-methyl]-phenoxy}-nicotinamidine

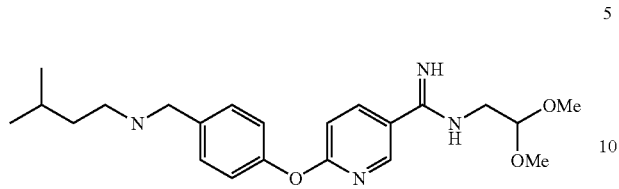

To a solution of the compound of Example 1 (1.0 equiv) in MeOH was added dropwise aminoacetaldehyde dimethyl acetal (1.0 equiv) and the mixture was heated at 70° C. for 1 hour and 30 min. The reaction was monitored by TLC. The solvent was removed under vacuum. It was purified by silica gel chromatography using CHCl$_3$:EtOH 7%:NH$_4$OH 0.7 to afford the title compound.

45% Yield 1H-NMR (CD$_3$OD, 300.00 MHz): 8.42 (d, J=2.8 Hz, 1H); 8.06 (dd, J=8.5, 2.4 Hz, 1H); 7.41 (d, J=8.5 Hz, 2H); 7.10 (d, J=8.5 Hz, 2H); 6.96 (d, J=8.5 Hz, 1H); 3.77 (s, 2H); 3.42 (s, 6H); 3.37 (s, 2H); 2.64-2.59 (m, 2H); 1.67-1.58 (m, 1H); 1.48-1.40 (m, 2H); 0.92 (d, J=6.5 Hz, 6H). MS (Electrospray): (M$^+$+1) 401.2

Step 2

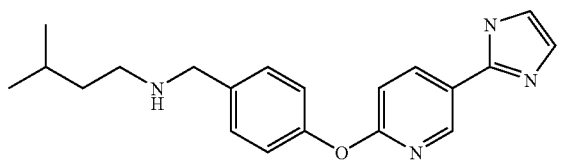

A solution of the amidine (Step 1) in formic acid was heated at 75° C. overnight. The reaction can be monitored by HPLC/electrospray MS. The solvent was removed under vacuum. It was purified by silica gel chromatography using CHCl$_3$:EtOH 7%:NH$_4$OH 0.7 to afford the title compound.

13% Yield 1H-NMR (CD3OD, 300.00 MHz): 8.61 (d, J=2.4 Hz, 1H); 8.24 (dd, J=8.9, 2.4 Hz, 1H); 7.42 (d, J=8.1 Hz, 2H); 7.16 (s, 2H); 7.12 (d, J=8.5 Hz, 2H); 7.02 (d, J=8.5 Hz, 1H); 3.78 (s, 2H); 2.65-2.60 (m, 2H); 1.65-1.58 (m, 1H); 1.48-1.41 (m, 2H); 0.92 (d, J=6.5 Hz, 6H). MS (Electrospray): (M$^+$+1) 337.1

Example 11

Synthesis of 6-{4-[3-Methyl-butylamino)-methyl]-phenoxy}-benzoisoxazol-3-ylamine Step 1

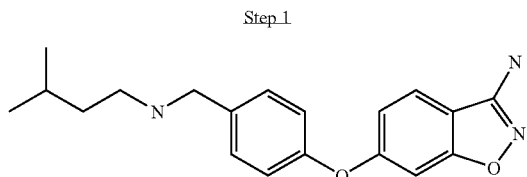

40

2-Fluoro-4-(4-formyl-phenoxy)-benzonitrile,
4-Fluoro-2-(4-formyl-phenoxy)-benzonitrile

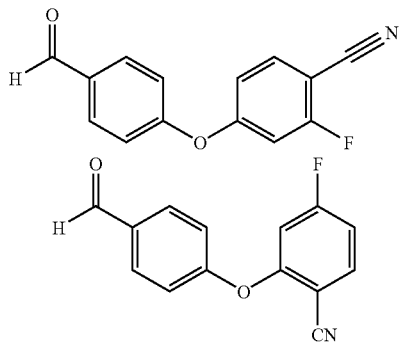

Combine 4-hydroxy-benzaldehyde (1 equiv), 2,4-Difluorobenzonitrile (1 equiv), and potassium carbonate (1.5 equiv) in dimethylformamide, (0.1 M) and warm to 130° C. After 3 h, cool to ambient temperature, dilute reaction mixture with water and extract with ethyl acetate (3×). Wash combined organic extracts with water and brine successively, dry over anhydrous magnesium sulfate, filter, and concentrate. Purify the residue by silica gel chromatography (hexanes:ethyl acetate 6:4) to provide a mixture of two compound as a white solid.

56% Yield 1H-NMR (CDCl3, 300.00 MHz): 10.01 (s, 2H); 7.97 (d, J=8.5 Hz, 4H); 7.72 (dd, J=8.9, 6.1 Hz, 2H); 7.62 (dd, J=8.5, 7.3 Hz, 2H); 7.22 (dd, J=8.9, 4.8 Hz, 4H); 6.97 (ddd, J=8.5, 7.7, 2.4 Hz, 2H); 6.91 (dd, J=8.5, 2.4 Hz, 2H); 6.87-6.83 (m, 1H); 6.70 (dd, J=9.3, 2.4 Hz, 2H).

Step 2

2-Fluoro-4-{4-[(3-methyl-butylamino)-methyl]-phenoxy}-benzonitrile

4-Fluoro-2-{4-[(3-methyl-butylamino)-methyl]-phenoxy}-benzonitrile

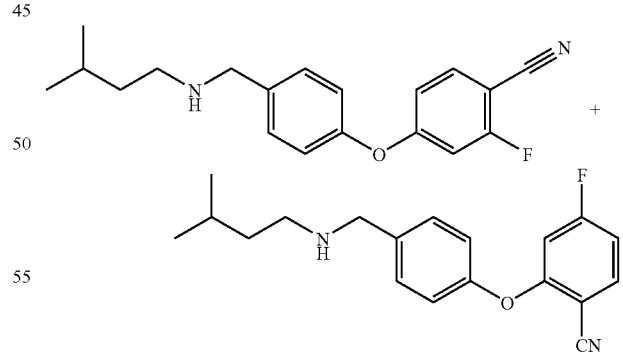

Add isoamylamine (1 equiv) to a solution of compound of Step 1 (1 equiv) in methanol. 4 Å molecular sieves (1000% weight) were added. The mixture was stirred overnight under nitrogen atmosphere at room temperature. The following day NaBH$_4$ (5 equiv) was added and the reaction mixture was stirred for 3 hours. The progress of the reaction can be monitored by TLC analysis. The reaction mixture was filtered off and the solvent evaporated to yield a residue which was purified by silica gel chromatography using CHCl₃:EtOH 7%:NH₄OH 0.7 to afford the title compound as an oil.

79% Yield 1H-NMR (CDCl3, 300.00 MHz): 7.64 (dd, J=8.9, 6.1 Hz, 1H); 7.53 (dd, J=8.9, 7.3 Hz, 1H); 7.40 (d, J=7.7 Hz, 4H); 7.08-7.02 (m, 4H); 6.81 (d, J=2.4 Hz, 1H); 6.81 (dd, J=16.1, 2.4 Hz, 1H); 6.71 (dd, J=10.5, 2.4 Hz, 1H); 6.50 (dd, J=10.1, 2.4 Hz, 1H); 3.81 (s, 4H); 2.66 (t, J=7.7 Hz, 4H); 1.69-1.58 (m, 2H); 1.46-1.39 (m, 4H); 0.90 (d, J=6.9 Hz, 12H).

Step 3

[4-(2-Cyano-5-fluoro-phenoxy)-benzyl]-(3-methyl-butyl)-carbamic acid tert-butyl ester

[4-(4-Cyano-3-fluoro-phenoxy)-benzyl]-(3-methyl-butyl)-carbamic acid tert-butyl ester

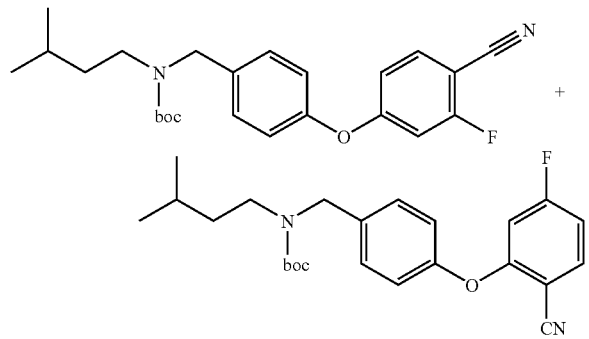

Add di-t-butyldicarbonate (1 equiv) to a solution of compound of Step 2 (1 equiv) in dichloromethane. The reaction mixture stirred overnight under nitrogen atmosphere at room temperature. The reaction can be monitored by TLC. Concentrate on a rotary evaporator to yield the crude product as a mixture of two compounds.

99% Yield 1H-NMR (CDCl3, 300.00 MHz): 7.64 (dd, J=8.9, 6.1 Hz, 1H); 7.53 (dd, J=8.5, 7.7 Hz, 1H); 7.30 (d, J=7.7 Hz, 4H); 7.05 (dd, J=11.3, 8.5 Hz, 4H); 6.85-6.79 (m, 2H); 6.71 (dd, J=10.9, 2.4 Hz, 1H); 6.50 (dd, J=10.1, 2.4 Hz, 1H); 4.43 (s, 4H); 3.18 (s, 4H); 1.48 (s, 24H); 0.89 (d, J=6.9 Hz, 12H).

Step 4

[4-(4-Cyano-3-isopropylideneaminooxy-phenoxy)-benzyl]-(3-methyl-butyl)-carbamic acid tert-buty-lester

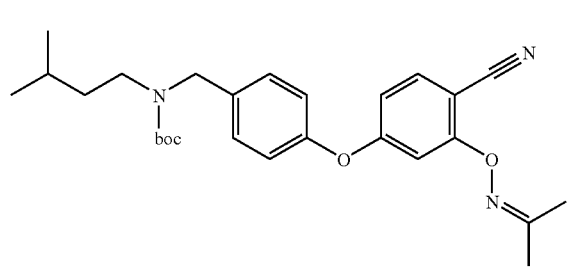

To a solution of acetone oxime (1.1 equiv) in DMF was added sodium tert-butoxide (1.1 equiv). The mixture was stirred at room temperature for 45 min followed by the addition of a solution of compound from Step 3 (1 equiv). The reaction was stirred at room temperature for 3 hours. It was poured on NH4Cl sat and ether. Washed with water and dry over magnesium sulphate, filtered and concentrate. It was purified by silica gel chromatography using hexane:ethyl acetate (15%) to afford the title compound as a white solid.

27% Yield 1H-NMR (CDCl3, 300.00 MHz): 7.44 (d, J=8.9 Hz, 1H); 7.25 (d, J=8.1 Hz, 2H); 7.15 (d, J=2.0 Hz, 1H); 7.01 (d, J=8.5 Hz, 2H); 6.53 (dd, J=8.5, 2.4 Hz, 1H); 4.42 (s, 2H); 3.17 (s, 2H); 2.13 (s, 3H); 2.00 (s, 3H); 1.47 (s, 12H); 0.88 (d, J=6.5 Hz, 6H).

Step 5

6-{4-[(3-Methyl-butylamino)-methyl]-phenoxy}-benzo[d]isoxazol-3-ylamine

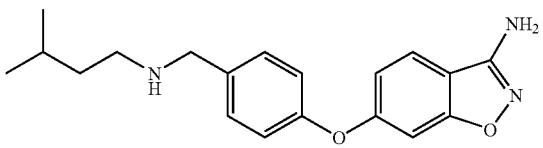

Add HCl 5% (1 mL) to a solution of compound of Step 4 (1 equiv, 0.1 mmol) in ethanol. The reaction mixture stirred at 80° C. for 2 hours. The reaction can be monitored by TLC. Concentrate on a rotary evaporator and basified with a solution of potassium carbonate. Extracted with ethyl acetate and wash with brine. Dry over magnesium sulphate filtered and concentrate. It was purified by silica gel chromatography using CHCl₃:EtOH 7%:NH₄OH 0.7 to afford the title compound as a white solid.

53% Yield MS (Electrospray): (M⁺+1) 326.1 1H-NMR (CD3OD, 300.00 MHz): 7.69 (d, J=8.9 Hz, 1H); 7.40 (d, J=8.5 Hz, 2H); 7.05 (d, J=8.5 Hz, 2H); 6.93 (dd, J=8.5, 1.6 Hz, 1H); 6.82 (d, J=2.0 Hz, 1H); 3.76 (s, 2H); 2.64-2.59 (m, 2H); 1.66-1.55 (m, 1H); 1.48-1.40 (m, 2H); 0.91 (d, J=6.9 Hz, 6H).

Example 12

6-{4-[(3,3-Dimethyl-butylamino)-methyl]-phenoxy}-benzo[d]isoxazol-3-ylamine

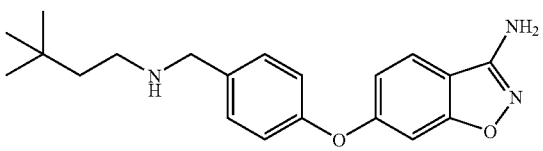

Using a similar method to Example 11 affords the title compound.

40% Yield MS (Electrospray): (M⁺+1) 340.2 1H-NMR (CD3OD, 300.00 MHz): 7.77 (d, J=8.5 Hz, 1H); 7.48 (d, J=8.5 Hz, 2H); 7.13 (d, J=8.5 Hz, 2H); 7.00 (d, J=8.5 Hz, 1H); 6.90 (s, 1H); 3.85 (s, 2H); 2.74-2.68 (m, 2H); 1.58-1.52 (m, 2H); 1.00 (s, 9H).

Example 13

6-(4-{[2-(4-Fluoro-phenyl)-ethylamino]-methyl}-phenoxy)-benzo[d]isoxazol-3-ylamine

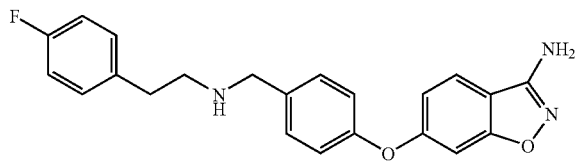

Using a similar method to Example 11 affords the title compound.

42% Yield MS (Electrospray): (M⁺+1) 378.1 1H-NMR (CD3OD, 300.00 MHz): 7.70 (d, J=8.7 Hz, 1H); 7.38 (d, J=8.7 Hz, 2H); 7.25-7.20 (m, 2H); 7.07-6.99 (m, 4H); 6.94 (dd, J=8.7, 2.0 Hz, 1H); 6.84 (d, J=1.6 Hz, 1H); 3.79 (s, 2H); 2.83 (s, 4H).

Example 14

6-(4-{[2-(Tetrahydro-pyran-4-yl)-ethylamino]-methyl}-phenoxy)-benzo[d]isoxazol-3-ylamine

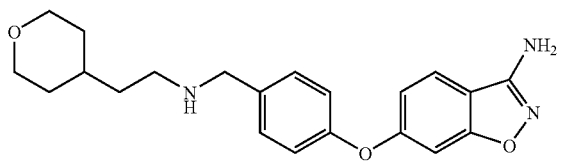

Using a similar method to Example 11 affords the title compound.

32% Yield MS (Electrospray): (M⁺+1) 368.1 1H-NMR (CD3OD, 300.00 MHz): 7.81 (d, J=8.5 Hz, 1H); 7.52 (d, J=8.9 Hz, 2H); 7.17 (d, J=8.9 Hz, 2H); 7.04 (dd, J=8.5, 2.0 Hz, 1H); 6.93 (d, J=1.6 Hz, 1H); 4.02 (dd, J=11.3, 4.4 Hz, 2H); 3.88 (s, 2H); 3.55-3.47 (m, 2H); 2.75 (t, J=7.7 Hz, 2H); 1.74-1.70 (m, 3H); 1.64-1.57 (m, 3H); 1.44-1.34 (m, 2H).

Example 15

6-{4-[(3-Methyl-butylamino)-methyl]-phenoxy}-1H-indazol-3-ylamine

Step 1

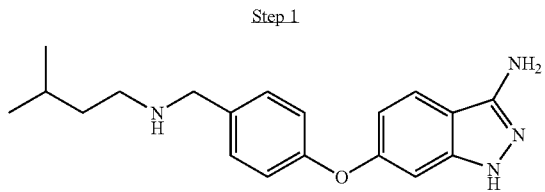

[4-(3-Amino-1H-indazol-6-yloxy)-benzyl]-(3-methyl-butyl)-carbamic acid tert-butyl ester

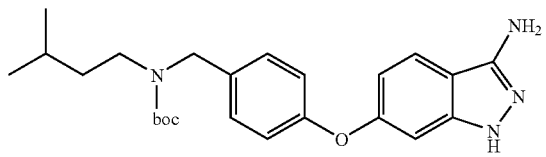

To a solution of the compound of Step 3 (Example 11) (1 equiv) in n-butanol was added hydrazine (3 equiv) and heated at reflux for 4 hours. The reaction was monitored by TLC. The reaction was cooled to ambient temperature and partitioned between ethyl acetate and water. The organic phase was washed with water and dried over sodium sulfate and filtered. The solvent was removed under vacuum. It was purified by silica gel chromatography using CHCl₃:10% (EtOH/10% NH₄OH) to afford the title compound.

26% Yield MS (Electrospray): (M⁺+1) 425.2 1H-NMR (CD3OD, 300.00 MHz): 7.42 (d, J=8.5 Hz, 1H); 7.24 (d, J=8.5 Hz, 2H); 7.03 (d, J=8.9 Hz, 2H); 6.50 (dd, J=8.5, 2.0 Hz, 1H); 6.23 (s, 1H); 4.42 (s, 2H); 3.15 (s, 2H); 1.47 (d, J=8.9 Hz, 12H); 0.88 (d, J=6.5 Hz, 6H).

Step 2

6-{4-[(3-Methyl-butylamino)-methyl]-phenoxy}-1H-indazol-3-ylamine

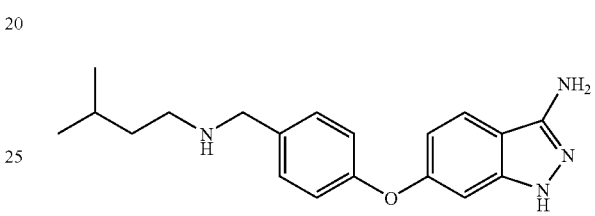

To a solution of compound of Step 1 (Example 15) (1 equiv) in CH2Cl2 was added trifluoroacetic acid (20 equiv) and stirred at room temperature for 3 hours. The reaction was monitored by TLC. It was purified by silica gel chromatography using CHCl₃:10% (EtOH/10% NH₄OH) to afford the title compound.

74% Yield MS (Electrospray): (M⁺+1) 325.1 1H-NMR (CD3OD, 300.00 MHz): 7.54 (s, 1H); 7.50 (d, J=8.5 Hz, 2H); 7.17 (d, J=8.5 Hz, 2H); 6.68 (dd, J=8.9, 2.0 Hz, 1H); 6.47 (d, J=2.0 Hz, 1H); 3.95 (s, 2H); 2.84-2.78 (m, 2H); 1.79-1.68 (m, 1H); 1.62-1.54 (m, 2H); 1.04 (d, J=6.4 Hz, 6H).

Example 16

6-{4-[(3-Methyl-butylamino)-methyl]-phenoxy}-nicotinic acid dihydrochloride

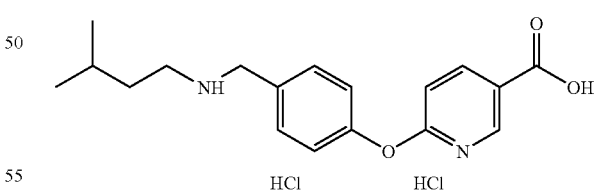

Combine 6-{4-[(3-Methyl-butylamino)-methyl]-phenoxy}-nicotinamide (0.46 g, 1.47 mmol) with 25 mL of aqueous 9N aqueous hydrochloric acid. Heat to reflux for 2 hours with stirring, then cool to room temperature overnight. Filter the precipitate, and wash with isopropyl alcohol. Dry the solid in vacuo to afford 0.31 g of the product (54% yield): ESMS (M⁺=315.22, free base), HNMR (DMSO-d6): 9.13 (br s, 2 H), 8.75 (s, 1 H), 8.30 (dd, 2 H), 7.6 (d, 2 H), 7.24 (d, 2 H), 7.14 (m, 1 H), 4.13 (br t, 2 H), 2.91 (br m, 2 H), 2.48 (m, 1 H), 1.5-1.67 (br m, 3 H), 0.86 (d, 6 H).

We claim:

1. A compound selected from the group consisting of:

6-{4-[(3-Methyl-butylamino)-methyl]-phenoxy}-nicotinimidic acid ethyl ester

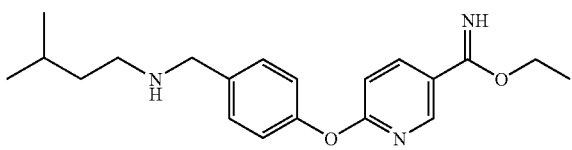

N-Hydroxy-6-{4-[(3-methyl-butylamino)-methyl]-phenoxy}-nicotinamidine

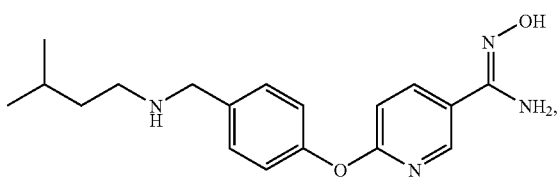

6-{4-[(3-Methyl-butylamino)-methyl]-phenoxy}-nicotinamidine

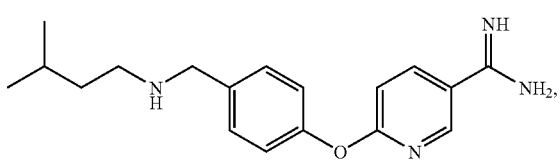

{4-[5-(4,5-Dihydro-1H-imidazol-2-yl)-pyridin-2-yloxy]-benzyl}-(3-methyl-butyl)-amine

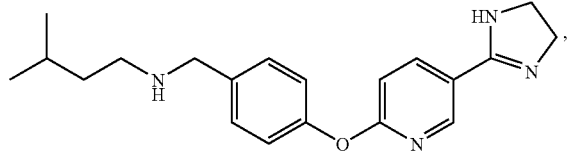

{4-[5-(4,5-Dihydro-1H-imidazol-2-yl)-pyridin-2-yloxy]-benzyl}-(2-thiophen-2yl-ethyl)amine

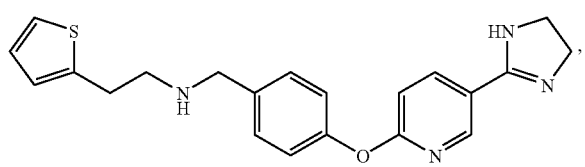

(3-Methyl-butyl)-{4-[5-(4,5,6,7-tetrahydro-1H-[1,3]diazepin-2-yl)-pyridin-2-yloxy]-benzyl}-amine

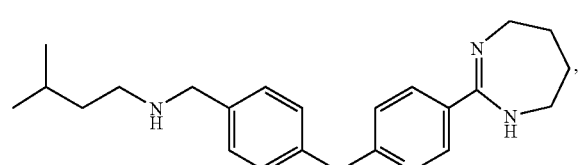

(3-Methyl-butyl)-{4-[5-(1,4,5,6-tetrahydropyrimidin-2-yl)-pyridin-2-yloxy]-benzyl}-amine

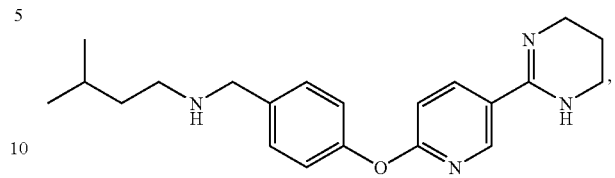

N-Cyano-6-{4-[(3-methyl-butylamino)-methyl]-phenoxy}-nicotinamidine

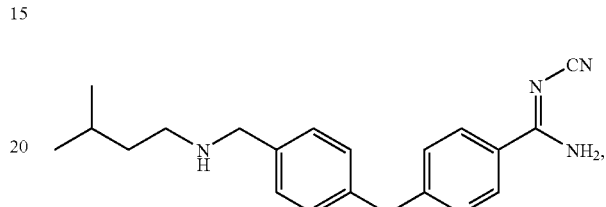

(3-Methyl-butyl)-{4-[5-(2H-tetrazol-5-yl)-pyridin-2-yloxy]-benzyl}-amine

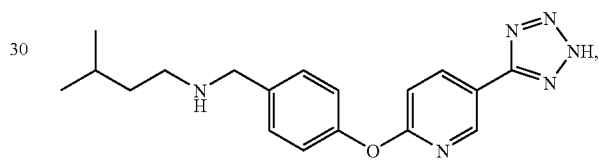

{4-[5-(1H-Imidazol-2-yl)-pyridin-2-yloxy]-benzyl}-(3-methyl-butyl)-amine

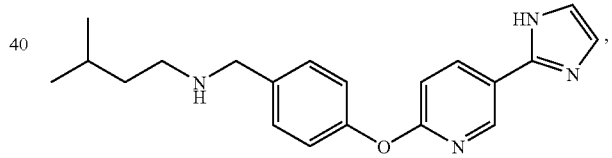

N-(2,2-Dimethoxy-ethyl)-6-{4-[(3-methyl-butylamino)-methyl]-phenoxy}-nicotinamidine

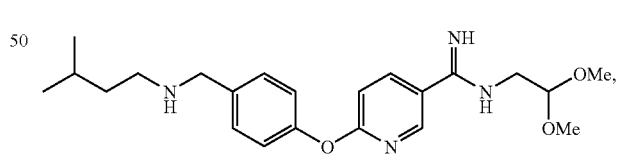

6-{4-[3-Methyl-butylamino)-methyl]-phenoxy}-benzoisoxazol-3-ylamine

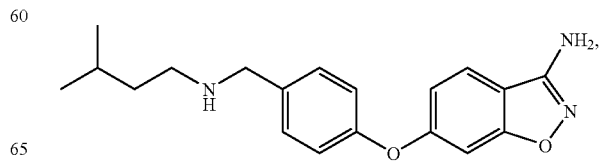

6-{4-[(3,3-Dimethyl-butylamino)-methyl]-phenoxy}-benzo[d]isoxazol-3-ylamine

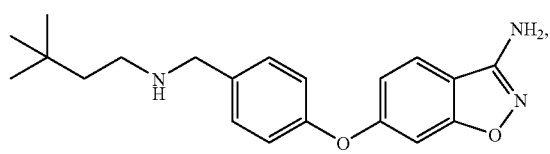

6-(4-{[2-(4-Fluoro-phenyl-ethylamino]-methyl}-phenoxy)-benzo[d]isoxazol-3-ylamine

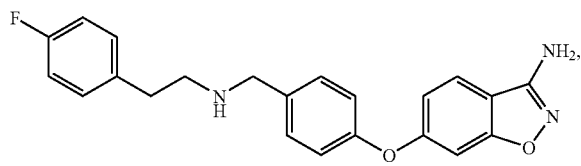

6-(4-{[2-(Tetrahydro-pyran-4-yl)-ethylamino]-methyl}-phenoxy)-benzo[d]isoxazol-3-ylamine

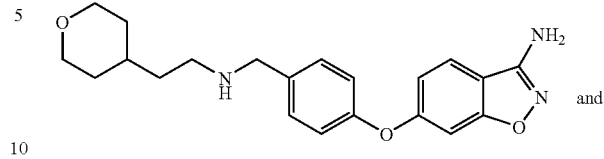

and

6-{4-[(3-Methyl-butylamino)-methyl]-phenoxy}-1H-indazol-3-ylamine

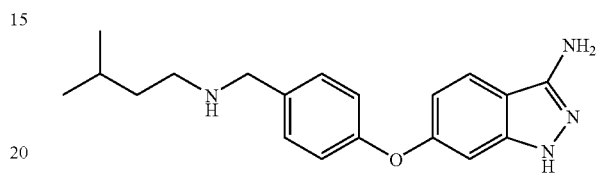

or a pharmaceutically acceptable salt thereof.

2. A pharmaceutical composition comprising a compound according to claim 1 in association with a carrier, diluent and/or excipient.

* * * * *

UNITED STATES PATENT AND TRADEMARK OFFICE
CERTIFICATE OF CORRECTION

| | | |
|---|---|---|
| PATENT NO. | : 7,414,132 B2 | Page 1 of 1 |
| APPLICATION NO. | : 10/581178 | |
| DATED | : August 19, 2008 | |
| INVENTOR(S) | : Marta Garcia De La Torre et al. | |

It is certified that error appears in the above-identified patent and that said Letters Patent is hereby corrected as shown below:

On the Title page:
Insert --(60) Related U.S. Application Data
Provisional application no. 60/539,748, filed January 28, 2004.--

Column 1, line 2, insert the following cross-reference after the title:
--This application is the national phase application, under
35 USC 371, for PCT/US2004/039766, filed December 15, 2004,
which claims the benefit, under 35 USC 119(e), of EP application
03380303.2, filed December 22, 2003, and US provisional
application 60/539,748, filed January 28, 2004.--

Signed and Sealed this
Twenty-second Day of February, 2011

David J. Kappos
*Director of the United States Patent and Trademark Office*